US008415105B2

(12) United States Patent
Schuren et al.

(10) Patent No.: US 8,415,105 B2
(45) Date of Patent: Apr. 9, 2013

(54) **METHOD OF DETECTING PATHOGENIC *LEGIONELLA* STRAINS**

(75) Inventors: Frank Henri Johan Schuren, Veenendaal (NL); Roy Christiaan Montijn, Amsterdam (NL); Henricus Matheus Wilhelmus Maria Thijssen, Houten (NL)

(73) Assignee: Nederlandse Organisatie voor toegepast-natuurwetenschappelijk Onderzoek TNO, Delft (NL)

( * ) Notice: Subject to any disclaimer, the term of this patent is extended or adjusted under 35 U.S.C. 154(b) by 0 days.

(21) Appl. No.: 12/521,119

(22) PCT Filed: Dec. 28, 2007

(86) PCT No.: PCT/NL2007/000332

§ 371 (c)(1), (2), (4) Date: Dec. 14, 2009

(87) PCT Pub. No.: WO2008/082290

PCT Pub. Date: Jul. 10, 2008

(65) Prior Publication Data

US 2010/0099577 A1 Apr. 22, 2010

(30) Foreign Application Priority Data

Dec. 29, 2006 (EP) .................................... 06077343

(51) Int. Cl.

*C12Q 1/68* (2006.01)
*C07H 21/02* (2006.01)
*C07H 21/04* (2006.01)

(52) U.S. Cl. ...... 435/6.15; 435/6.1; 435/6.11; 536/23.1; 536/23.7; 536/24.32

(58) Field of Classification Search ........................ None
See application file for complete search history.

(56) References Cited

FOREIGN PATENT DOCUMENTS

| | | |
|---|---|---|
| WO | WO-92/11273 | 7/1992 |
| WO | WO-94/28174 | 12/1994 |
| WO | WO-2005/049642 | 6/2005 |

OTHER PUBLICATIONS

International Search Report for PCT/NL2007/000332, mailed on Jun. 9, 2008, 3 pages.
International Preliminary Report on Patentability for PCT/NL2007/000332, issued on Jun. 30, 2009.
Database GenBank, Acccession No. CP000675, May 25, 2007.
Harrison et al., Clinical Microbiology and Infection (2007) 13:78-85.
Ko et al., Journal of Microbiological Methods (2003) 54(3):325-337.
Steinert et al., International Journal of Medical Microbiology (2007) 297(7-8):577-587.

*Primary Examiner* — Carla Myers
(74) *Attorney, Agent, or Firm* — Morrison & Foerster LLP

(57) ABSTRACT

The invention relates to a method of detecting pathogenic *Legionella pneumophila* strains by hybridizing genomic DNA of a sample suspected to contain *Legionella* to two or five specific sequence markers, as identified by MARKER NO. 1 through MARKER NO. 5 or homologues thereof. The invention further relates to a kit of parts comprising an array and reference materials for performing a method of the invention.

5 Claims, No Drawings

SEQUENCE LISTING

<160> NUMBER OF SEQ ID NOS: 13

<210> SEQ ID NO 1
<211> LENGTH: 1710
<212> TYPE: DNA
<213> ORGANISM: Legionella pneumophila

<400> SEQUENCE: 1

```
aaaggagact tggcagctct caagaacttg tttggttgca agcaaaaact tcaacccggc     60

tctctaatta gccttgataa tacaaccttt gcctttcctt gtaagggagt tcctacccaa    120

tactgggatc tggtaaatgg ctgggaatta caaaacaagg tatctatagg tgaacccatt    180

aaatggtcgg atattaagca aaaaaatgat tgttaaaaac cctacttgga actctcttac    240

ccctccactt cctaaatttg tttcttgtga tacaggcgag acaaatttcc tgaaagaaaa    300

attaggagaa gatgggaggg tttttattgc tcaatttgat ctaaaatcca cctctgcttt    360

tttatttcag cgtaaaagtg atcaaaaaaa attttttatc aagaaagtat ccgctgaaca    420

taaaagacag tatcagcaga gcgaacattt ggctcaattt atcgcttgcc cagattatat    480
```

-continued

```
agttaatatt gcaattaact gcgtttctaa tgaagaagaa aactcactct attatattta    540
tccctatatt catggaaaac gcctctttgc tgaaccagag gaaataataa gccttgcaac    600
tgcattagca aaattacatc ttaaaaaaaa atcttatcct gatcaacaat tgattattaa    660
aaatactacg gaacgaacat cacagcttaa ttttataaga aaggctttag ctaatggatg    720
ttattcctac attccatatt tctcttttgt taaaaagatg gctcaacaat atgattttga    780
ttggattaat caagaagatg cccaaccaat tcatggtgat ttaaatgcag gaaatctgtt    840
actatccgaa aataatatga tttgcttttt tgactttgaa gacgcattac atagtttcca    900
tccagtagta ttagatttgc tattcgtcat tgagcgtatt atttttaatc aaaatagttc    960
gactgaacgg ctattaaacc ttggtctcat gtttattcat gcatataaaa aggctggtgg   1020
tacataccgg tataaaacga gagatgaatt tggattaaca attcttgctt taaaagcatt   1080
ttgcttgttg actttgctag cagagaaaaa taaaaatata ctgaactcgg aatgggataa   1140
attttttaaa ttaactcaga aagcagaaaa tgaacgggat ttaataaaaa caattttaca   1200
aggataagaa agatagtgtg agagttcttg ttactgcacg ggatgttggt gctgcattaa   1260
acattattga gatagtaaaa atacttaaac aatatacagg tgttactgta tatatttatg   1320
ctcaacctcc cgcttcaaaa tattttcttc gggctgggat tcaatctgta tttcaagttc   1380
cactaccacc aacccgatcc tcaaatgaat ccaatcatct actatcctac gccaatcaat   1440
taattgataa attaaatccc gatatcatat tatctggatt atcatctcct ggcgaagctg   1500
gcatagatga agcaataata gctgtgtgtc ccgcgcatat caaaacattc atccttcaag   1560
atttttgggg agaagttaat tttttctttg aaaaattagc ggattgctat ttatgcatag   1620
atcatcacgc tgcagaaatt acaaaaaaac gatttaatgc caaaaccagg gtgataggct   1680
cccctcgcca taccattttc aaacataaaa                                   1710
```

<210> SEQ ID NO 2
<211> LENGTH: 1714
<212> TYPE: DNA
<213> ORGANISM: Legionella pneumophila

<400> SEQUENCE: 2

```
aaaggagtac ttggcagctc tcaaagaact tgtttggttg caaagcaaaa acttcaaccc     60
ggctctctaa ttagccttga taatacaacc tttgcctttc cttgtaaggg agttcctacc    120
caatactggg atctggtaaa tggctgggaa ttacaaaaca aggtatctat aggtgaaccc    180
attaaatggt cggatattaa gcaaaaaaat gattgttaaa aaccctactt ggaactctct    240
taccccctcca cttcctaaat ttgtttcttg tgatacaggc gagacaaatt tcctgaaaga    300
aaaattagga gaagatggga gggtttttat tgctcaattt gatctaaaat ccacctctgc    360
ttttttattt cagcgtaaaa gtgatcaaaa aaaatttttt atcaagaaag tatccgctga    420
acataaaaga cagtatcagc agagcgaaca tttggctcaa tttatcgctt gcccagatta    480
tatagttaat attgcaatta actgcgtttc taatgaagaa gaaaactcac tctattatat    540
ttatccctat attcatggaa aacgcctctt tgctgaacca gaggaaataa taagccttgc    600
aactgcatta gcaaaattac atcttaaaaa aaaatcttat cctgatcaac aattgattat    660
taaaaatact acggaacgaa catcacagct taattttata agaaaggctt tagctaatgg    720
atgttattcc tacattccat atttctcttt tgttaaaaag atggctcaac aatatgattt    780
tgattggatt aatcaagaag atgcccaacc aattcatggt gatttaaatg caggaaatct    840
gttactatcc gaaaataata tgatttgctt ttttgacttt gaagacgcat tacatagttt    900
```

ccatccagta gtattagatt tgctattcgt cattgagcgt attattttta atcaaaatag 960
ttcgactgaa cggctattaa accttggtct catgtttatt catgcatata aaaaggctgg 1020
tggtacatac cggtataaaa cgagagatga atttggatta acaattcttg ctttaaaagc 1080
attttgcttg ttgactttgc tagcagagaa aaataaaaat atactgaact cggaatggga 1140
taaatttttt aaattaactc agaaagcaga aaatgaacgg gatttaataa aaacaatttt 1200
acaaggataa gaaagatagt gtgagagttc ttgttactgc acgggatgtt ggtgctgcat 1260
taaacattat tgagatagta aaaatactta aacaatatac aggtgttact gtatatattt 1320
atgctcaacc tcccgcttca aaatattttc ttcgggctgg gattcaatct gtatttcaag 1380
ttccactacc accaacccga tcctcaaatg aatccaatca tctactatcc tacgccaatc 1440
aattaattga taaattaaat cccgatatca tattatctgg attatcatct cctggcgaag 1500
ctggcataga tgaagcaata atagctgtgt gtcccgcgca tatcaaaaca ttcatccttc 1560
aagatttttg ggagaagtt aatttttct ttgaaaaatt agcggattgc tatttatgca 1620
tagatcatca cgctgcagaa attacaaaaa aacgatttaa tgccaaaacc agggtgatag 1680
gctcccctcg ccataccatt tatcaaacat taaa 1714

<210> SEQ ID NO 3
<211> LENGTH: 1446
<212> TYPE: DNA
<213> ORGANISM: Legionella pneumophila

<400> SEQUENCE: 3
ttcttcattc catctctggc accagatttt acctaaaact tcatgccaaa tcttagcaag 60
ctttggaata cagtctgaat attgttttag gtaggctatt gttatcatca taatacctgt 120
ttaaaatgga ttattcctcg cactcgtggc aaggcgttcc ttgatgaaac accatttgcc 180
aacgattgtg tttgtattgc cagagcgaag aacgtaaaga actttttgag gcaacagtaa 240
ccttataagt tgccaacatg acttcaggcg acacctctaa aactgaaaaa tcattaacca 300
tatagcttcg ttgctcttct tctggaagag aatcaagtag gtcgttctta ttgtaaattg 360
agccagaggc cccatactcg ataaattcat cagcaatcaa tagtttcagt tgcgcaatag 420 atttctcgt ttccgacctt aatagagaaa tttctagctc ataaatcaat tggtgttctt 480
gtttcatagc gattttctca tcaaataaac gttgaaatcc aaaaaacaat tatgctctgt 540
catggatatg acaacatacc caagctgttc ataaaaagat cttgcctgaa attcggccgt 600
ctcaatggta atcacttggc aattcttttg ttttgcaaaa atttccagtt tttccatgag 660
atttcgtcct aatccttttt gtctaaaatc cggatgaacc caaatgcaat cgacatagca 720
attggctcga gtgacatccc cataacaacc tgctaaaacg gtcttgtcga tagattttat 780
atagatggta aagggagtat gattgtaagc accaatcatt tcttcattgt agatctttaa 840
gccgtcagat aaaatggcag tgatttcttg gttggttcgt tcttcgaaac aaatctcata 900
gtcattgttc ttggctaaaa ttataagctc tggtattttt gcatcttctg gtgcatcgga 960
atgataaccg ctccaaagaa tacctccata aggttgtagt attttttcaa ccaacttttt 1020
taaatgagtt gaatcacctt ccttataaac tcgattaaaa ctttcagaaa actccctggc 1080
taaatcggga ttttcttgat gcaaatagcg aatgattgat ttaccactgg cgcaccattt 1140
attttgagct ctaaaataaa attgagacaa tgcttcaaaa agccatgagg ctgaggcaat 1200
ttgttcttca taagacttag gagataaaat atcttctaag acatccgtaa ttaaaaaacg 1260
ctctttatca atttgatttt tatcccaaga aagaggtccg cgctttaagt aaagataggc 1320

-continued

```
ctcctctcta atcccgtttg aaaaatcgct agctggcatc atatcttttc ccgacaaaat   1380

catttgaatg gttcctgaaa taccggaatt tattctcgat tctcaaaaaa ataacgaatg   1440

gtttct                                                              1446


<210> SEQ ID NO 4
<211> LENGTH: 1450
<212> TYPE: DNA
<213> ORGANISM: Legionella pneumophila

<400> SEQUENCE: 4

ttcttcaatt ccaatctctg gcatccagat tttacctaaa acttcatgcc aaatcttagc     60

aagctttgga atacagtctg aatattgttt taggtaggct attgttatca tcataatacc    120

tgtttaaaat ggattattcc tcgcactcgt ggcaaggcgt tccttgatga aacaccattt    180

gccaacgatt gtgtttgtat tgccagagcg aagaacgtaa agaacttttt gaggcaacag    240

taaccttata agttgccaac atgacttcag gcgacacctc taaaactgaa aaatcattaa    300

ccatatagct tcgttgctct tcttctggaa gagaatcaag taggtcgttc ttattgtaaa    360

ttgagccaga ggccccatac tcgataaatt catcagcaat caatagtttc agttgcgcaa    420

tagattttct cgtttccgac cttaatagag aaatttctag ctcataaatc aattggtgtt    480

cttgtttcat agcgattttc tcatcaaata aacgttgaaa tccaaaaaac aattatgctc    540

tgtcatggat atgacaacat acccaagctg ttcataaaaa gatcttgcct gaaattcggc    600

cgtctcaatg gtaatcactt ggcaattctt ttgttttgca aaaatttcca gtttttccat    660

gagatttcgt cctaatcctt tttgtctaaa atccggatga acccaaatgc aatcgacata    720

gcaattggct cgagtgacat ccccataaca acctgctaaa acggtcttgt cgatagattt    780

tatatagatg gtaaagggag tatgattgta agcaccaatc atttcttcat tgtagatctt    840

taagccgtca gataaaatgg cagtgatttc ttggttggtt cgttcttcga aacaaatctc    900

atagtcattg ttcttggcta aaattataag ctctggtatt tttgcatctt ctggtgcatc    960

ggaatgataa ccgctccaaa gaatacctcc ataaggttgt agtatttttt caaccaactt   1020

ttttaaatga gttgaatcac cttccttata aactcgatta aaactttcag aaaactccct   1080

ggctaaatcg ggattttctt gatgcaaata gcgaatgatt gatttaccac tggcgcacca   1140

tttattttga gctctaaaat aaaattgaga caatgcttca aaaagccatg aggctgaggc   1200

aatttgttct tcataagact taggagataa aatatcttct aagacatccg taattaaaaa   1260

acgctcttta tcaatttgat ttttatccca agaaagaggt ccgcgcttta agtaaagata   1320

ggcctcctct ctaatcccgt ttgaaaaatc gctagctggc atcatatctt ttcccgacaa   1380

aatcatttga atggttcctg aaataccgga atttattctc gattcttcaa aaaaataacg   1440

aatggattct                                                          1450


<210> SEQ ID NO 5
<211> LENGTH: 891
<212> TYPE: DNA
<213> ORGANISM: Legionella pneumophila

<400> SEQUENCE: 5

cagctgattc gtttttctgg gatatgtctt ggcatgcaga tgatgctttc caaagtactg     60

aatttggaca acatgaaggt ctgggtctaa ttgctggcga ggttgttagc gtcccttcac    120

atggagttga tggtcaattg cataaaatac ctcatatagg ctggaatgaa ctggtttcca    180

cctcggaagg cgaggattgg tgtcatacta tcctgaaaaa tataccatta aattcttcag    240
```

```
tatattttgt tcattctttt atggccatgc ctagtaatcc taaaaagcgt ctggctgata    300

ctttatatga tggtcaggct attagcgcag taataaaaga tgaaaatatg tacggatgcc    360

aatttcatcc tgaaaaaagc ggggaagtag gtttaagcat cattcaacag tttttgcaga    420

tttagggtga attaaaaatg agaatattgg cagtaatccc ggcaagggct ggctcaaaga    480

ggctgcccgg taaaaatacc agattacttg ccggaaaacc attaattgca catactattg    540

ttgctgcctt gcagtcgtct tgttgtgaag aaatcgttgt ttcgaccgat agtaaacaaa    600

tagcagacgt cgcagttcaa tatggggctt cagtaccctg gctaagatcg gaagatttag    660

ccacggatac ttcggatgtg attcatactg ttattgacct cctgtttaag tttcagcaaa    720

tggaggtttt ttttgacagt gtattgctgt tacaaccaac ttctccattt aggaagccag    780

aaaccataag acatgctgtt gaaatacatc aagtaacggg gaaaagtgtc gtttcagtta    840

gtcccatctc tttaaagcct tcttggtgta gaagcattga tagccaaggc a             891
```

<210> SEQ ID NO 6
<211> LENGTH: 881
<212> TYPE: DNA
<213> ORGANISM: Legionella pneumophila

<400> SEQUENCE: 6

```
tgccttggct atcaatgctt ctacaccaag aaggctttaa agagatggga ctaactgaaa     60

cgacactttt tcccgttgct tgatgtattt caacagcatg tcttatggtt tctggcttcc    120

tgaatggaga agttggttgt aaaagcaata cactgtcaaa aaaaacctcc atttgctgaa    180

acttaaacag gaggtcaata acagtatgaa tcacatccga agtatccgtg gctaaatctt    240

ccgatcttag ccagggtact gaagccccat attgaacggc gacgtctgct atttgtttac    300

tatcggtcga aacaacgatt tcttcacaac aagacgactg caaggcagca acaatagtat    360

gtgcaattaa tggttttccg gcaagtaatc tggtattttt accgggcagc ctctttgagc    420

cagcccttgc cgggattact gccaatattc tcatttttaa ttcaccctaa atctgcaaaa    480

actgttgaat gatgcttaaa cctacttccc cgcttttttc aggatgaaat tggcatccgt    540

acatattttc atcttttatt actgcgctaa tagcctgacc atcatataaa gtatcagcca    600

gacgcttttt aggattacta ggcatggcca taaaagaatg aacaaaatat actgaagaat    660

ttaatggtat atttttcagg atagtatgac accaatcctc gccttctgag gtagaaacca    720

gttcattcca gcctatatga ggtattttat gcaattgacc atcaactcca tgtgaaggga    780

cgctaacaac ctcgccagca attagaccca gaccttcatg ttgtccaaat tcagtacttt    840

tggaaagcat catctgcatg ccaagacata ttcccagaaa a                        881
```

<210> SEQ ID NO 7
<211> LENGTH: 1034
<212> TYPE: DNA
<213> ORGANISM: Legionella pneumophila
<220> FEATURE:
<221> NAME/KEY: misc_feature
<222> LOCATION: (627)..(627)
<223> OTHER INFORMATION: n is a, c, g, or t
<220> FEATURE:
<221> NAME/KEY: misc_feature
<222> LOCATION: (720)..(720)
<223> OTHER INFORMATION: n is a, c, g, or t
<220> FEATURE:
<221> NAME/KEY: misc_feature
<222> LOCATION: (773)..(773)
<223> OTHER INFORMATION: n is a, c, g, or t

<400> SEQUENCE: 7

-continued

```
atacaccgcc gcccatgagc cgttcaaagc tgtagtgaag tatttacaag agcatatcag     60
taaagccatc acttcaggca acgttgaaag ccttcatgat caagtgctca ttgatctgtt    120
tgatgcggcc attatggata aaaattatta cgataaaatc acagccagtg ttggccctgt    180
attatcagag attaataaga gtaatgcctc caggatcttt tcatttcata aaagcaattg    240
tgaaatcgag ttgatgagtg caataaaaaa caaacaagtc atctatatcg ggctggatag    300
cttaacaaac cccaatatcg ctcaagcagt cggtaaagcc tttttgtcag atttagtatc    360
cactgctgga aaaatatata aggaaagtaa cgcgaattac cgtctcaatc tccattgcga    420
tgagctttct gaaattatcc aagattcgtt tgttaaaatt ttaaataaag ccggtggagc    480
tggtttccaa gtcacagctt atgctcagac caaacaaaat atggaggtag cgctaggttc    540
aaaagccaaa gcagaagtga ctgaaggaaa tctaaacacc ctcatcatgt tacgtgtcaa    600
aaatgaagaa actgccaatt tattagntta aagttttacc aaaaatttgg cgtggtcgaa    660
catactcaag tctccatggt caacgacaca ccccatggcg aagatgggcg tttattttan    720
caccaccaat gaagatcgtg tacaaaccac cgcagtgccg atgaattgat gtncatgaca    780
ttatctcatt accccaaggg caagcatttt gttttagtga atgggcggaa gaactgtaca    840
aagtaagaat acccttaccc tgtgacgatg gattagcccc caagggatat caaaagcgct    900
attcgtgtaa ttaaccaaat tggatgataa ccttggagat taatatgaaa gcagaaatta    960
ctttaaaccc ttcgtacccg tgaagtgtac aagttatttg aaagaaagat taatgaggat   1020
agattattta ttga                                                     1034
```

```
<210> SEQ ID NO 8
<211> LENGTH: 1031
<212> TYPE: DNA
<213> ORGANISM: Legionella pneumophila

<400> SEQUENCE: 8

acggaaatac accaccgccc atgagtcgtt caaaatctgt ggtgaagtat ttacaagagc     60
atatcagtaa agccatcact tcaggcaatg ttgaaagcct tcatgatcaa gtactcattg    120
atctgtttga tgctgccatc atggacaaaa attattacga taaaatcacg gccagtgtcg    180
gccctgtgtt atcagaaatt aataaaagta atgcatcaaa gatcttttca tttcataaaa    240
gcaattgtga aatcgagttg atgagtgcaa taaaaaacaa acaagtcatt tatatcggac    300
tggatagctt aacaaacccc aatatcgccc aagcagtagg taaagccttt ttgtcagatt    360
tagtatccac agctggaaaa atatataagg aaagtaacgc gaattaccgt ctcaatctcc    420
attgcgatga actttctgaa atcatccaag actcatttgt caaaatttta aataaagccg    480
gtggagctgg ttttcaagtc accgcttatg ctcagaccaa acaagatatg gaggtggcat    540
taggctctaa agccaaagca gaagtgactg aaggaaatct aaatacgctc atcatgttac    600
gtgttaaaaa tgaagaaaca gccaatttat tagttaaagt gttaccaaaa attggcgtgg    660
tcgagcacac tcaagtgtcc atggtcaacg acacacccca tggcgaggat ggcgtttatt    720
ttaacaccac caatgaagat cgagtacaaa ccaccgcagt acctatgatt gatgtcaatg    780
acattatctc attgcccaaa gggcaagcct ttgttttagt gaatggcgga gagctgtaca    840
aagtaagaat acccttacct gtgaacgatg gattagcccc caaggatatc aaaagcgcta    900
ttcgtgcaat taaccaattg gatgataacc ttggagatta atatgaaagc agaaattact    960
ttaaaccttc gtacccgtga agtgtataaa ttatttgaga ggaaaattag tggggatagg   1020
ttatttattg a                                                        1031
```

<210> SEQ ID NO 9
<211> LENGTH: 531
<212> TYPE: DNA
<213> ORGANISM: Legionella pneumophila

<400> SEQUENCE: 9
attgcgggtt aaatatttta ctgaatcgca aaccacttaa taacgataag aagcccgata 60
ccaaaacacc catgacgcat acttggccaa cacctgctga tgccagtaaa tgggcagtta 120
aagtattagg tgatattcat gtaagcaccg ctacagatgc agataaaacc aaacacgatg 180
ccaaagctgg cattggatta tccgcgttat tgcaaagttg tgacagctcc aacacctgta 240
cttcaaatgt gtctaaagca ctgtggaatc tagtagacaa gcaatggccg ttgactgaag 300
aaaaactcaa aatggttagt gcatccaact tgatgattac agatgaaatt atcatcacca 360
tacaacgtat gccgcgggaa gagcaaattt taactgtttc caaattggct gaggaaattg 420
ctgtacaaaa catgctcgat aaggccttga tgatgcgccg tatcttacaa gctggtcttc 480
aagtacaaga agtacaaaac ttaaagcccg cgcttgatat ggtgaaattt g 531

<210> SEQ ID NO 10
<211> LENGTH: 526
<212> TYPE: DNA
<213> ORGANISM: Legionella pneumophila

<400> SEQUENCE: 10
cgttcgaaaa accaccagat gccataggta ttgcaggaat atccctatta taaacagacc 60
gcaaatactg cctaacgcct tagggttata accacttaga gccaaaatca caggagtcaa 120
tataatcagg aagaaataca aaaaggcctg catgacaggt agtgtttgca taatagcttc 180
acgctttaat ggcgttgatg tccatgattt tgttaattgc ccaatattta ctaacccatg 240
agaaatggca ccaccaaaag ccccattagt gtttcccatt aggtttttca tactgttagc 300
ctgcatgtcg cgactgtcat taagcaacat cttggcaatg tagtcttctg agcttaactg 360
cgaaccccag gctttgggat ggtcattttt gaatgtgcgt accctgtcta aaaccgcgta 420
gtaattcagg tggctgtcaa agacactggc gttattggct acttgcacca aatctgtttt 480
gagctttttc caccattgat tgcaggtggg atagccttgc tctggc 526

<210> SEQ ID NO 11
<211> LENGTH: 2055
<212> TYPE: DNA
<213> ORGANISM: Legionella pneumophila

<400> SEQUENCE: 11
attgcgggtt acaatatttt actgaatcgc aaaccactta ataatgaaaa gaagcccgat 60
actaaaacac ccatgacgca tacttggcca acacctgctg atgccagtaa atgggcagtt 120
aaagtattag gtgatattca tgtaagcacc gctacagatg cagataaaac caaacacgat 180
gccaaagctg gcattggatt atccgcgtta ttgcaaagtt gtgacagctc caacacctgt 240
acttccaatg tgtctaaagc actgtggaat ctagtagaca agcaatggcc gttgactgaa 300
gaaaaactca aaatggttag tgcatccaac ttgatgatta cagatgaaat catcatcacc 360
atacaacgta tgccgcggga agaacaaatc ttaactgttt ccaaattggc cgaggaaatt 420
gctgtacaaa acatgctcga taaggccttg atgatgcgcc gtattttaca agctggtctt 480
caagtacaag aagtacaaaa cttaaagccc gcgcttgata tggtgaaatt tgccttaaag 540
aaactcgatg atgacattca ttctttatct tttgaaagcg aagtccgtaa aaaaatgatg 600

-continued

```
actgaaacct taggtctttt gatggatatg cgaggtagcg atatagccaa gggcttgcct     660

ggtgaagatc atgaacaatc gcaagttaaa aatggcgcag tctatgcgaa acctgattcc     720

aaaggagcat aagatggttg tatttagccc tttatccttg tacaccacct atttaggctg     780

gcagcaatat gaggttattt ttaatgccct gtggcaaacc ggtttgttat accttggttt     840

tcttatggta gggtatcgat tcttaaaaaa tgtgctggca ccttctggtg ctacacatca     900

cgcggcagaa tatgccttga atcattttct ttatgaattg gcaattactt ttttgatttg     960

cggcatcttt atctacccct gtgtgccatt ggaagaaaaa gccatgagtt ttaagcctat    1020

gtgcggtata aaaaaaggaa cagatgcaaa aacctctacg ttaaaagata caggtactac    1080

ttatgatgaa gcatttgcag acgtactgac ccccaatgtc aaaatgccta ttggttttgc    1140

actcttgcaa aattacatgt cagggattac ctacggcttg atgaaagtga ccggttgcac    1200

cgacagctta caagcaattg aaggcgattt aatttccacc tatttacctg ccgatgtacg    1260

tgagcaagca ttgaattttc acagacaatg cttccttgag gccagaagcc aatatcacaa    1320

tgaaccgcac gataaaacta aggtcaatga cattttaaaa aaatacggtg gtgaggaaga    1380

tttgaaatgg gtgggttcca aagtctatca aacactatac tatgataaaa tttacgcaag    1440

acaacccgta gctggcttta cctttaacga agcccccaac aaaaatctcg aaaaagcagc    1500

agaacgtggt gatattgatg ccaaacatct gccagagcaa ggctatccca cctgcaatca    1560

atggtggaaa aagctcaaaa cagatttggt gcaagtagcc aataacgcca gtgtctttga    1620

cagccacctg aattactacg cggttttaga cagggtacgc acattcaaaa ataaccatcc    1680

caaagcctgg ggttcgcagt taagctcaga agactacatt gccaagatgt tgcttaatga    1740

cagtcgcgac atgcaggcta acagtatgaa aaacctaatg ggaaacacca atggggcttt    1800

tggtagtgcc atttctcatg ggttagtaaa tattgggcaa ttaacaaaat catggacatc    1860

aacgccatta aagcgtgaag ccattatgca aacgctacct gtcatgcagg ctttttttgta   1920

tttcttcctg attatcttga ctcctgtgat tttggctcta agtggttata accctaaggc    1980

gttaggcagt atttgcggtc tgtttatcat ggcgattttc ctgcaatacc tgtggcatct    2040

ggtgggtttt gtcga                                                     2055
```

<210> SEQ ID NO 12
<211> LENGTH: 866
<212> TYPE: DNA
<213> ORGANISM: Legionella pneumophila
<220> FEATURE:
<221> NAME/KEY: misc_feature
<222> LOCATION: (52)..(52)
<223> OTHER INFORMATION: n is a, c, g, or t

<400> SEQUENCE: 12

```
ataaagagat atttctttgc gcaatgcaaa gtagtcaagc attacatcat cnttgggtta      60

aagcgcctgt aacacctgat gagtttgatg agtatttttc tcgctatcaa aaacccaaac     120

ccaaaaaagt ttctgctttt ttctgccaat aacttagcgg gcgtctttaa tatcagcgaa     180

atagtacgtg gttactttca aaatgcgtat ttgggctttt atgctgttga ggctcatgcg     240

ggtaaaggat acatgagtaa gggtttaaaa ttaatattaa ccaggatttt taaggaaatg     300

gggttgcatc ggttagaggc gaatatacaa cctgaaaata accgttcaat ctggctggtg     360

aagaaaaatg gttttcgtta tgaaggattt tctccacgtt atttgagggt gaatgatgtg     420

tggcaaggtc atgagcattg ggccatgact tatgaagatt ttatcaagga taataatgat     480

gtgcttgaaa aagatcatat cgacattgtt gcctataata ccgagtggcc actgctagct     540
```

-continued

```
aaaatagaaa tggcgaaatt acgcgcttca tttccagcca atagtgtgat tgatctccag    600

catgtgggta gtacagcaat acctggcatg gcagcaaaac ccattattga tattcagatt    660

gcagccaggt cattggagga aatgaagatt attgctgtgc cgatattaca gaaattaggt    720

tatgaatatt gggaagataa tccggactct gaacgaatgt tctttgtaaa aggcatgcca    780

ccctatggta atgggcgaac acaccatgtt catattgttg aaacatcatc caggcatgga    840

aaggaaagat actttcagag actatt                                         866


<210> SEQ ID NO 13
<211> LENGTH: 867
<212> TYPE: DNA
<213> ORGANISM: Legionella pneumophila

<400> SEQUENCE: 13

ataaagagat gtttctttgt gctatgcaaa gtagtcaagc attacatcat ccttgggtta     60

aggcaccgat aatacctgaa gagtttgatg agtatttttc tcgctatcaa aaaccaaacc    120

aaaaaagcta tctgcttctt tctgacaata acttagcggg tgtctttaat atcagtgaaa    180

tagtacgtgg ttactttcag aatgcgtatt tgggctttta tgttgttgca gcttatgcgg    240

gtaaaggata tatgagtact ggtttgaaat taatattaac caaagttttt aaggacatgg    300

ggttgcatcg cttagaagcg aatatacaac ctgagaatac ccgttcaatc tggcttgtga    360

agaaaaatgg ttttcgctat gaaggatttt ccccacgata tttgagagtg aatgacgtgt    420

ggcaaggtca tgagcattgg gccatgactt atgaagattt tatcaaggat aataatgagg    480

tacttgaaaa agatcatatc gatattgttg catacaatac agagtggccg cttctagcca    540

aggcagaaat ggtgaagtta cgcgcctcat ttcccgcaaa tagtgttatt gatatccagc    600

atgtaggcag tacagcaata cctggcatgg catcaaaacc cattattgat attcagattg    660

cagtgaggtc attagaagaa atgaagatta ttgctgtgcc gatattacag aaattagatt    720

atgaatattg ggaagataat ccagatcctg aacgaatgtt ttttgtaaaa ggcatgcccc    780

cctatggtaa tggacgaacg caccatgttc atatcgtcga agcatcatcc aggcattgga    840

aaggaaaaac atttttcaga gactatt                                        867
```

METHOD OF DETECTING PATHOGENIC *LEGIONELLA* STRAINS

CROSS-REFERENCE TO RELATED APPLICATIONS

This application is the national phase of PCT application PCT/NL2007/000332 having an international filing date of 28 Dec. 2007, which claims benefit of European application No. 06077343.9 filed 29 Dec. 2006. The contents of the above patent applications are incorporated by reference herein in their entirety.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
|---|---|---|
| 313632007000Seqlist.txt | Dec.14, 2009 | 21,318 bytes |

FIELD OF THE INVENTION

The invention relates to a method of typing *Legionella pneumophila* strains, and in particular to a method of identifying a *Legionella pneumophila* strain as being either pathogenic or non-pathogenic. The invention further relates to markers for such an assay and a kit of parts comprising an array with said markers and reference materials for performing a method of the invention.

BACKGROUND OF THE INVENTION

Legionnaires' disease is an acute pneumonic illness caused by Gram-negative bacilli of the genus *Legionella*, the most common of which is *Legionella pneumophila.*

Legionnaires' disease is initiated by inhalation, and probably microaspiration, of *Legionella* bacteria into the lungs. Although *Legionella* bacteria are ubiquitous in our environment, they rarely cause disease. A number of factors must occur simultaneously before legionnaires' disease is possible. These factors include the presence of virulent strains in an environmental site; a means for dissemination of the bacteria, such as by aerosolization; and proper environmental conditions allowing the survival and inhalation of an infectious dose of the bacteria by a susceptible host.

Water contaminated with a sufficient concentration of virulent *Legionella* bacteria can be aerosolized by water-cooled heat rejection devices such as air conditioning cooling towers, whirlpool spas, shower heads, water misters, and the like. Once the bacteria enter the lung, they are phagocytosed by alveolar macrophages and then grow intracellularly. The *Legionella* bacteria produce virulence factors that enhance phagocytosis. After sufficient intracellular growth, the bacteria kill the macrophage, escape into the extracellular environment and are then rephagocytosed by other macrophages. Within a few days after initial infection, the bacterial concentration in the lung increases considerably. The resulting infiltration of the alveoli by neutrophils, additional macrophages and erythrocytes results in capillary leakage and edema and the chemokines and cytokines released by the macrophages help trigger a severe inflammatory response, which may be fatal.

More than 49 different *Legionella* species, encompassing 70 serogroups, have been described since its first discovery in 1977, 20 of which have been reported to infect humans. *L. pneumophila* contains at least 16 different serogroups. *L. pneumophila* serogroup 1 caused the 1976 Philadelphia outbreak and is the cause of 70% to 90% of all cases of legionnaires' disease. In the major outbreaks such as those originating in Bovenkarspel, The Netherlands in 1999, in Barrow-in-Furness in Cumbria, England in 2002 and near Harnes in Pas-de-Calais, France in 2003/2004, serogroup 1 strains could be detected in the majority of the patients.

*L. pneumophila* serogroup 1 can be further divided into multiple subtypes using a variety of serologic, other phenotypic and genetic methods. One particular subtype of *L. pneumophila* serogroup 1 causes the majority of cases of legionnaires' disease due to *L. pneumophila*, and 85% of the cases due to *L. pneumophila* serogroup 1; this subtype is distinguished by its reactivity with a particular monoclonal antibody, and it is variously termed Pontiac, the Joly monoclonal type 2 (MAb2), or the Dresden monoclonal type 3/1 (MAb 3/1) monoclonal subtype.

Most clinical microbiology laboratories are capable of identifying *Legionella* bacteria to the genus level by detection of their typical colony morphology, Gram stain appearance, and various other standard microbiology identification techniques. Identification of *L. pneumophila* serogroup 1, the most common clinical isolate can be accomplished by sophisticated clinical microbiology laboratories using relative simple serologic testing. However, it should be stressed that serogroup 1 strains are not the only virulent serotypes. Identification of other *L. pneumophila* serogroups, and other *Legionella* species, is often much more difficult. This is because these bacteria are relatively inert in the use of commonly tested biochemical substrates, and they require sophisticated phenotypic, serologic and molecular testing. Reference laboratory-based phenotypic testing of bacteria, including determination of fatty-acids and ubiquinones and protein electrophoresis, can often be used to identify the bacteria. Definitive identification is based on both immunologic detection of surface antigens and bacterial DNA sequencing. Also, DNA typing by pulsed field electrophoresis of DNA restriction fragments is useful for identification purposes.

Diagnosis of the infecting agent from clinical material (such as sputum or bronchoalveolar lavage fluid) on selective media is currently the most reliable means of diagnosis. However, cultivation is slow. Direct fluorescent antibody (DFA) stains for the visualization of *Legionella* species in clinical specimens are commercially available for a limited number of species. Assays for the detection of *L. pneumophila* serogroup 1 antigen in urine have a sensitivity of 70% and a specificity of nearly 100%. Also, an immunochromatographic assay for the rapid qualitative detection of *L. pneumophila* serogroup 1 antigen (*Legionella* NOW; Binax, Portland, Me.) in urine specimens has become available that uses rabbit anti-*L. pneumophila* serogroup 1 antibody as the capture component and rabbit anti-*L. pneumophila* serogroup 1 antibody conjugated to colloidal gold as the detection component. The assay provides a test result in 15 min and is intended to aid in the presumptive diagnosis of Legionnaires' disease caused by *L. pneumophila* serogroup 1 in conjunction with culture and other methods. Preliminary performance data for the immunochromatographic assay report a sensitivity of 95% and a specificity of 95%. Thus, so far, commercially available tests for *Legionella* urinary antigen detect only *L. pneumophila* serogroup 1, while the specificity of the assays cannot prevent the occurrence of false positive and false negative reactions.

DNA probe techniques, which produce fewer false positive reactions then immunological detection methods, may be used to detect the presence of one or more multiple *Legionella* species. However, a drawback of such DNA methods is that they cannot differentiate between virulent and non-virulent strains, presumably because the virulence trait is multi-genic.

Following severe outbreaks, many national authorities have implemented legislation and water quality standards for water supplies and/or codes of practice for management and operation of cooling towers and warm water storage facilities. Such standards and codes require frequent monitoring of drinking water distribution systems and swimming-pool water facilities, and upon exceeding a certain number of *Legionella* bacteria per liter, rigorous measures are taken, such as closure and evacuation of hotels, sports facilities or nursing homes. Most experts however, consider that a large number of *Legionella* bacteria detected are harmless and non-virulent. However, there is at present no assay system available to distinguish between virulent and non-virulent strains and it is difficult to avoid the costs involved with false-alarm *Legionella* detection. The availability of a test that is capable of reliably detecting pathogenic *Legionella* strains would be highly favorable.

It is an object of the present invention to provide for a method capable of distinguishing between clinically relevant and environmental strains of *L. pneumophila*. It is a further object of the present invention to provide a method of detecting pathogenic *Legionella* strains including, but not limited to serogroup 1 strains.

SUMMARY OF THE INVENTION

The present inventors have now found a method for distinguishing between clinical or pathogenic strains and environmental or non-pathogenic *Legionella* strains. The method involves an hybridization assay with specific genetic markers.

In one embodiment of the present invention, the group of molecular markers comprises the two markers MARKER NO. 1 and MARKER NO. 2, having sequences 1a, 1b and 2a and 2b, respectively, or sequences which are highly homologous to those.

In a preferred embodiment of the method of the present invention, the group of molecular markers comprises the five markers MARKER NO. 1, MARKER NO. 2, MARKER NO. 3, MARKER NO. 4 and MARKER NO. 5, having the sequences as presented in the sequence listing or homologues thereof.

In a further embodiment of the method of the present invention, the sample nucleic acid is derived from a pure culture of *Legionella pneumophila*. Alternatively, the sample can be derived from any medium which is suspected of *Legionella* infestation, such as aqueous samples from water pipes, surface water, drink water, showers, baths, fountains, etc.

A kit of parts, said kit comprising an array as defined herein together with reference nucleic acids as defined herein. Preferably, said kit also comprises software to calculate the result of the test.

DETAILED DESCRIPTION OF THE INVENTION

The term "*Legionella pneumophila* strain" as used herein refers to the descendants of a single isolate of *Legionella pneumophila* cells in pure culture and to a taxonomic level of said pure culture below the level of the species *Legionella pneumophila*.

The term "pathogenic" in relation to a *Legionella* strain refers to a microorganism capable of causing disease (including infection) or morbid symptoms in humans or other animal hosts.

The term "array" refers to an array of individual fragments of DNA or oligonucleotides that are bound to a substrate such as a microscope slide. The purpose of an array experiment is to determine the amount of matching nucleic acid fragments in a particular sample. The target nucleic acid fragments are extracted from the cells or tissues of interest, optionally converted to DNA, and labeled. They are then hybridized to all the DNA or oligonucleotide spots on the array. Matches (i.e. the spots where hybridization has taken place) are identified using antibody detection, optionally combined with precipitation, chromatography, colorimetry, and/or phosphorescent or fluorescent imaging. The data resulting from an array experiment are a list of measurements of spot intensities. A preferred array of the invention is an array which has less than 1000, preferably less than 100, more preferably less than 50 and most preferably less than 10 spots, and which contains at least the DNA sequences of MARKER NO. 1 and MARKER NO. 2. Another preferred array of the invention is an array which has less than 1000, preferably less than 100, more preferably less than 50 and most preferably less than 10 spots, and which contains at least the five sequences as presented in MARKER NO. 1 through MARKER NO. 5.

The term "nucleic acid" as used herein, is interchangeable with the term "polynucleotide", and refers to a nucleotide multimer or polymeric form of nucleotides having any number of nucleotides, e.g., deoxyribonucleotides or ribonucleotides, or compounds produced synthetically (e.g. PNA as described in U.S. Pat. No. 5,948,902 and the references cited therein) and can be either double- or single-stranded. A polynucleotide can hybridize with other polynucleotides in a sequence specific manner, e.g. can participate in Watson-Crick base pairing interactions. The term also includes modified, for example by methylation and/or by capping, and unmodified forms of the polynucleotide The terms "deoxyribonucleic acid" and "DNA" as used herein mean a polymer composed of deoxyribonucleotides.

The term "oligonucleotide" refers to a short sequence of nucleotide monomers (usually 6 to 100 nucleotides) joined by phosphorous linkages (e.g., phosphodiester, alkyl and aryl-phosphate, phosphorothioate), or non-phosphorous linkages (e.g., peptide, sulfamate and others). An oligonucleotide may contain modified nucleotides having modified bases (e.g., 5-methyl cytosine) and modified sugar groups (e.g., 2'-O-methyl ribosyl, 2'-O-methoxyethyl ribosyl, 2'-fluoro ribosyl, 2'-amino ribosyl, and the like). Oligonucleotides may be naturally-occurring or synthetic molecules of double- and single-stranded DNA and double- and single-stranded RNA with circular, branched or linear shapes and optionally including domains capable of forming secondary structures (e.g., stem-loop, pseudo knots and kissing loop structures).

The term "nucleotide sequence homology" as used herein denotes the presence of homology between two polynucleotides. Polynucleotides have "homologous" sequences if the sequence of nucleotides in the two sequences is the same when aligned for maximum correspondence. Sequence comparison between two or more polynucleotides is generally performed by comparing portions of the two sequences over a comparison window to identify and compare local regions of sequence similarity. The comparison window is generally from about 20 to 200 contiguous nucleotides. The "percentage of sequence homology" for polynucleotides, such as 50, 60, 70, 80, 90, 95, 98, 99 or 100 percent sequence homology may be determined by comparing two optimally aligned sequences over a comparison window, wherein the portion of the polynucleotide sequence in the comparison window may include additions or deletions (i.e. gaps) as compared to the reference sequence (which does not comprise additions or deletions) for optimal alignment of the two sequences. The percentage is calculated by: (a) determining the number of positions at which the identical nucleic acid base occurs in both sequences to yield the number of matched positions; (b) dividing the number of matched positions by the total number of positions in the window of comparison; and (c) multiplying the result by 100 to yield the percentage of sequence homology. Optimal alignment of sequences for comparison may be conducted by computerized implementations of known algorithms, or by visual inspection. Readily available sequence comparison and multiple sequence alignment algorithms are, respectively, the Basic Local Alignment Search Tool (BLAST) (Altschul et al., 1990; Altschul et al., 1997) and ClustalW programs, both available on the internet. Other suitable programs include, but are not limited to, GAP, BestFit, PlotSimilarity, and FASTA in the Wisconsin Genetics Software Package (Genetics Computer Group (GCG), Madison, Wis., USA) (Devereux et al., 1984).

As used herein, "highly homologous" means that two nucleic acid sequences have at least about 85%, preferably at least 90%, more preferably at least 92%, even more preferably at least 95%, and most preferably at least 98%, sequence complementarity to each other. This means that primers and probes must exhibit sufficient complementarity to their template and target nucleic acid, respectively, to hybridise under stringent conditions. Therefore, the primer and probe sequences need not reflect the exact complementary sequence of the binding region on the template and degenerate primers can be used. For example, a non-complementary nucleotide fragment may be attached to the 5'-end of the primer, with the remainder of the primer sequence being complementary to the strand. Alternatively, non-complementary bases or longer sequences can be interspersed into the primer, provided that the primer has sufficient complementarity with the sequence of one of the strands to be amplified to hybridize therewith, and to thereby form a duplex structure which can be extended by the polymerising means. The non-complementary nucleotide sequences of the primers may include restriction enzyme sites. Appending a restriction enzyme site to the end(s) of the target sequence would be particularly helpful for cloning of the target sequence. A substantially complementary primer sequence is one that has sufficient sequence complementarity to the amplification template to result in primer binding and second-strand synthesis. The skilled person is familiar with the requirements of primers to have sufficient sequence complementarity to the amplification template.

The term "hybrid" in the context of nucleic acids refers to a double-stranded nucleic acid molecule, or duplex, formed by hydrogen bonding between complementary nucleotide bases. The terms "hybridise" or "anneal" refer to the process by which single strands of nucleic acid sequences form double-helical segments through hydrogen bonding between complementary bases.

The term "probe" refers to a single-stranded oligonucleotide sequence that will recognize and form a hydrogen-bonded duplex with a complementary sequence in a target nucleic acid sequence analyte or its cDNA derivative.

The term "primer" as used herein refers to an oligonucleotide which is capable of annealing to the amplification target allowing a DNA polymerase to attach, thereby serving as a point of initiation of DNA synthesis when placed under conditions in which synthesis of primer extension product is induced, i.e., in the presence of nucleotides and an agent for polymerisation such as DNA polymerase and at a suitable temperature and pH. The (amplification) primer is preferably single stranded for maximum efficiency in amplification. Preferably, the primer is an oligodeoxyribonucleotide. The primer must be sufficiently long to prime the synthesis of extension products in the presence of the agent for polymerisation. The exact lengths of the primers will depend on many factors, including temperature and composition (A/T en G/C content) of primer. A pair of bi-directional primers consists of one forward and one reverse primer as commonly used in the art of DNA amplification such as in PCR amplification.

It will be understood that "primer", as used herein, may refer to more than one primer, particularly in the case where there is some ambiguity in the information regarding the terminal sequence(s) of the target region to be amplified. Hence, a "primer" includes a collection of primer oligonucleotides containing sequences representing the possible variations in the sequence or includes nucleotides which allow a typical base pairing.

The oligonucleotide primers may be prepared by any suitable method. Methods for preparing oligonucleotides of specific sequence are known in the art, and include, for example, cloning and restriction of appropriate sequences, and direct chemical synthesis. Chemical synthesis methods may include, for example, the phospho di- or tri-ester method, the diethylphosphoramidate method and the solid support method disclosed in e.g. U.S. Pat. No. 4,458,066. The primers may be labelled, if desired, by incorporating means detectable by for instance spectroscopic, fluorescence, photochemical, biochemical, immunochemical, or chemical means.

Template-dependent extension of the oligonucleotide primer(s) is catalysed by a polymerising agent in the presence of adequate amounts of the four deoxyribonucleotide triphosphates (dATP, dGTP, dCTP and dTTP, i.e. dNTPs) or analogues, in a reaction medium which is comprised of the appropriate salts, metal cations, and pH buffering system. Suitable polymerizing agents are enzymes known to catalyse primer- and template-dependent DNA synthesis. Known DNA polymerases include, for example, *E. coli* DNA polymerase I or its Klenow fragment, T4 DNA polymerase, and Tag DNA polymerase. The reaction conditions for catalysing DNA synthesis with these DNA polymerases are known in the art.

The products of the synthesis are duplex molecules consisting of the template strands and the primer extension strands, which include the target sequence. These products, in turn, serve as template for another round of replication. In the second round of replication, the primer extension strand of the first cycle is annealed with its complementary primer; synthesis yields a "short" product which is bound on both the 5'- and the 3'-ends by primer sequences or their complements. Repeated cycles of denaturation, primer annealing, and extension result in the exponential accumulation of the target region defined by the primers. Sufficient cycles are run to achieve the desired amount of polynucleotide containing the target region of nucleic acid. The desired amount may vary, and is determined by the function which the product polynucleotide is to serve.

The PCR method is well described in handbooks and known to the skilled person.

After amplification by PCR, the target polynucleotides may be detected by hybridisation with a probe polynucleotide which forms a stable hybrid with that of the target sequence under stringent to moderately stringent hybridisation and wash conditions. If it is expected that the probes will be essentially completely complementary (i.e., about 99% or greater) to the target sequence, stringent conditions will be used. If some mismatching is expected, for example if variant strains are expected with the result that the probe will not be completely complementary, the stringency of hybridisation may be lessened. However, conditions are chosen which rule out non-specific/adventitious binding. Conditions which affect hybridisation, and which select against non-specific binding are known in the art, and are described in, for example, Sambrook et al., (2001). Generally, lower salt concentration and higher temperature increase the stringency of binding. For example, it is usually considered that stringent conditions are incubations in solutions which contain approximately 0.1×SSC, 0.1% SDS, at about 65° C. incubation/wash temperature, and moderately stringent conditions are incubations in solutions which contain approximately 1-2×SSC, 0.1% SDS and about 50°-65° C. incubation/wash temperature. Low stringency conditions are 2×SSC and about 30°-50° C.

The terms "stringency" or "stringent hybridisation conditions" refer to hybridisation conditions that affect the stability of hybrids, e.g., temperature, salt concentration, pH, formamide concentration and the like. These conditions are empirically optimised to maximize specific binding and minimize non-specific binding of primer or probe to its target nucleic acid sequence. The terms as used include reference to conditions under which a probe or primer will hybridise to its target sequence, to a detectably greater degree than other sequences (e.g. at least 2-fold over background). Stringent conditions are sequence dependent and will be different in different circumstances. Longer sequences hybridise specifically at higher temperatures. Generally, stringent conditions are selected to be about 5° C. lower than the thermal melting point (Tm) for the specific sequence at a defined ionic strength and pH. The Tm is the temperature (under defined ionic strength and pH) at which 50% of a complementary target sequence hybridises to a perfectly matched probe or primer. Typically, stringent conditions will be those in which the salt concentration is less than about 1.0 M Na+ ion, typically about 0.01 to 1.0 M Na+ ion concentration (or other salts) at pH 7.0 to 8.3 and the temperature is at least about 30° C. for short probes or primers (e.g. 10 to 50 nucleotides) and at least about 60° C. for long probes or primers (e.g. greater than 50 nucleotides). Stringent conditions may also be achieved with the addition of destabilizing agents such as formamide. Exemplary low stringent conditions or "conditions of reduced stringency" include hybridisation with a buffer solution of 30% formamide, 1 M NaCl, 1% SDS at 37° C. and a wash in 2×SSC at 40° C. Exemplary high stringency conditions include hybridisation in 50% formamide, 1 M NaCl, 1% SDS at 37° C., and a wash in 0.1×SSC at 60° C. Hybridisation procedures are well known in the art and are described by e.g. Ausubel et al., 1998 and Sambrook et al., 2001.

The term "fragmented genomic DNA" refers to pieces of DNA of the genome of a cell that are the result of the partial physical, chemical or biological break-up of the lengthy DNA into discrete fragments of shorter length.

The term "hybridization pattern" refers to the list of measurements of spot intensities obtained after hybridizing the array with a target nucleic acid.

The term "nucleotide" is used to denote a deoxyribonucleoside, a ribonucleoside, or a 2'-O-substituted ribonucleoside residue The term "molecular marker" generally refers to markers identifying variation at the level of DNA and is herein used to refer to a mutation (of any type) or nucleotide sequence which has a scorable or selectable relation with either the pathogenic or non-pathogenic phenotype (and hence can "mark" a region of the chromosome).

It now has been found, from a series of experiments comparing pathogenic and non-pathogenic *Legionella* strains, that a good discrimination can be achieved by detecting the presence of at least two marker sequences. Said markers are indicated as the sequences of MARKER NO. 1: sequences 1a (SEQ ID NO: 1) and 1b (SEQ ID NO: 2) and MARKER NO. 2: sequences 2a (SEQ ID NO: 3) and 2b (SEQ ID NO: 4). Sequences 1a and 1b form part of a larger DNA fragment, which in total can be said to be functioning as the MARKER NO. 1 in the present invention. For detection of the presence of said MARKER NO. 1, it is sufficient if either or both of the sequences 1a and 1b are detected. A similar indication is also used for sequences 2a and 2b, which can be said to be part of the MARKER NO. 2. In a typical experiment said markers are present on a hybridization array and DNA of a *Legionella* strain to be classified as pathogenic or non-pathogenic is allowed to hybridize with said markers. Thus, for detecting the presence of MARKER NO. 1 and MARKER NO. 2, both sequence 1a and/or 1b and sequence 2a and/or 2b can be present on said array.

In another embodiment of the present invention, the array comprises at least the five MARKERS NOS. 1-5. The sequences of MARKERS NOS. 1 and 2 are discussed above. The sequences of MARKER NO. 3 are sequence 3a (SEQ ID NO: 5) and sequence 3b (SEQ ID NO: 6). MARKER NO. 4 is characterized by 5 sequences: 4a (SEQ ID NO: 7), 4b (SEQ ID NO: 8), 4c (SEQ ID NO: 9), 4d (SEQ ID NO: 10) and 4e (SEQ ID NO: 11). MARKER NO. 5 again is characterized by two sequences, 5a (SEQ ID NO: 12) and 5b (SEQ ID NO: 13). As indicated above, this does not necessarily mean that all of the sequences of a specific marker need to be present on the array: the assay on pathogenicity can equally well been performed with sequences, which are parts of the MARKERS NOS. 1-5. It should, however, be understood, that a minimal length is necessary for obtaining a correct and distinctive hybridization with any sample nucleic acid. Thus, the length of these part(s) of the sequences should range from about 50 to about 2000 nucleotides, i.e. the sequences can be shorter or longer than those presented in the sequence listing, but for a sufficient hybridization to occur they should be at least 50 nucleotides long. In other words: the presence of marker no. 4 can be detected by performing an assay with either sequence 4a, 4b, 4c, 4d and 4e, or with any combination of those sequences. Longer sequences than those depicted can be obtained by hybridizing the genome from a *Legionella* species and, if hybridization occurs with the presented sequence, excise a larger part of the sequence from the genomic DNA.

Further, hybridization allows for some mismatches between the sequence on the array and the nucleotide sequence of the sample. Therefore, any nucleotide sequence or part thereof (as defined above) which has a homology of at least 85%, preferably at least 90%, more preferably at least 92%, more preferably at least 95%, even more preferably at least 99% with the sequences of SEQ ID NO: 1 through SEQ ID NO: 13 is applicable in and intended within the scope of the present invention.

In the current invention the term "homologues" is used to indicate both parts of the sequences of the invention of at least 50, but preferably at least 100, more preferably at least 200, more preferably at least 500 and most preferably at least 1000 nucleotides, and sequences, which have a degree of homology of at least 85%, preferably at least 90%, more preferably at least 92%, more preferably at least 95%, even more preferably at least 99% with the sequences of SEQ ID NO: 1 through SEQ ID NO: 13.

The above discussed markers, or fragments thereof (such as the sequences of SEQ ID NO: 1 through SEQ ID NO: 13) may be spotted on a surface to provide for a DNA micro-array. In order to facilitate coupling of the fragments, the surface of the array (e.g. the slide, the surface of which may i.a. be glass, gold, etc.) may be modified. Spotting may occur by any method available, for instance by using ElectroSpray Ionization (ESI) micro-array printing. After spotting of the markers or fragments thereof, the slide surfaces may be blocked to prevent further attachment of nucleic acids, e.g. by treatment with boro-anhydride in case of formaldehyde modified glass-slide surfaces.

To facilitate detection of successful hybridization, the gDNA is suitably labeled, preferably with a compound which is uniquely detectable by an antibody. Such a compound can for instance be biotin. Labeling of nucleotides with biotin and subsequent detection through antibodies specific for biotin, has been sufficiently described in the literature and will be routine experimentation for a person skilled in the art. Alternatively, the nucleotides are fluorescently labeled (e.g. by using Cy™ labels [Amersham Pharmacia Biotech]). Fluorescent labeling kits are commercially available from various manufacturers. In order to be able to judge the signals caused by the hybridization of the marker sequences with sample nucleic acid, preferably the array also comprises reference nucleotide sequences, which can serve as positive and negative controls. As negative controls, sequences should be used of about the same length as the average length of the markers, but which will not hybridize with any nucleotide sequence in the sample, i.e. sequences, which do not occur in *Legionella*. As positive control, a sequence should be used which will be present in (nearly) all samples to be tested. For this purpose preferably the *Legionella* 30S ribosomal protein S21 (Cazalet, C., Rusniok, C., Bruggemann, H., Zidane, N., Magnier, A., Ma, L., Tichit, M., Jarraud, S., Bouchier, C., Vandenesch, F., Kunst, F., Etienne, J., Glaser, P. and Buchrieser, C. Nat. Genet. 36 (11), 1165-1173 (2004)) or a conserved sequence of one of the housekeeping enzymes should be used.

The average size of sample nucleic acid has an effect on the signal distribution on the array. Larger sample molecules comprise more information and are thus more likely to find a suitable hybridization partner in more of the spots. Reducing the average size of the sample nucleic acid can reduce this phenomenon. On the other hand, when the sample nucleic acid is too small, the nucleic acid fragments in the sample contain too little genetic information and also find suitable hybridization partners in many spots. The average size of the fragments in the sample nucleic acid is preferably between about 30 and 3000 nucleotides. More preferably, the average size of the fragments in the sample nucleic acid comprises a size of between about 50 and 1000 nucleotides, more preferably between about 100 and 500 nucleotides.

In a method for detecting a pathogenic *L. pneumophila* strain, the sample nucleic acid may represent the whole or a part of the sample genome. Preferably, at least those parts of the genome are present in which the presence of molecular markers as defined herein is to be detected. This can be achieved by randomly digestion of the genomic DNA of the sample to fragments of about 1.5 kb or by physically fragmenting the DNA (e.g. by shearing) to form fragments of about that size. In a preferred embodiment a PCR amplification step is performed on either the intact genomic DNA or on the fragmented DNA with primers that specifically cause amplification of one or more of the sequences of the invention. Alternatively, the DNA can be randomly (primer) labeled using Klenow DNA polymerase (BioPrime kit Invitrogen) according to the manufacturer's instructions.

The fragmented sample DNA is then brought into contact with the array of the invention, which contains at least the two marker sequences MARKER NO. 1 and MARKER NO. 2 or fragments thereof (such as the sequences of SEQ ID NO: 1 through SEQ ID NO: 4), or homologues of said markers or fragments thereof, or, in another embodiment, the five marker sequences of the inventions or fragments thereof (such as the sequences of SEQ ID NO: 1 through SEQ ID NO: 13), or homologues of said markers or fragments thereof. Hybridization of the sample nucleotides with the marker sequences and the hybridization signals with optional positive and negative control sequences is then determined. Then, the diagnosis whether or not the sample contained a pathogenic *Legionella* strain is done according to the following logic rule for the assay with only MARKER NO. 1 and MARKER NO. 2. In said rule the value for MARKER NO. 1 or 2 is 1 if a positive hybridization signal is obtained with respect to said sequence, and it is 0 if no positive hybridization signal is detected.

If (MARKER NO. 1>MARKER NO. 2) then Pathogenic else Environmental

For the assay with all five sequences, the following set of 7 rules is applicable. If 4 or more of these rules are TRUE if the stochastic 0 or 1 value for each hybridization is entered, then the sample can be classified as pathogenic.

If (MARKER NO. 2<MARKER NO. 1) then [not (MARKER NO. 2=MARKER NO. 3)] else [(MARKER NO. 2=MARKER NO. 4) and (MARKER NO. 5=MARKER NO. 3)]

If (MARKER NO. 2<MARKER NO. 3) then [not (MARKER NO. 1<MARKER NO. 4)] else [(MARKER NO. 5>MARKER NO. 2) nor (MARKER NO. 5<MARKER NO. 4)]

If (MARKER NO. 2<MARKER NO. 3) then [not (MARKER NO. 4<MARKER NO. 1)] else [(MARKER NO. 3<MARKER NO. 5) nor (MARKER NO. 4>MARKER NO. 5)]

If (MARKER NO. 1=MARKER NO. 5) then [(MARKER NO. 4<=MARKER NO. 1)] else [(MARKER NO. 1<MARKER NO. 4) nor (MARKER NO. 3=MARKER NO. 2)]

If (MARKER NO. 1=MARKER NO. 5) then [(MARKER NO. 5>=MARKER NO. 4)] else [(MARKER NO. 3<=MARKER NO. 2) nor (not(MARKER NO. 4<MARKER NO. 1))]

If (MARKER NO. 1=MARKER NO. 5) then [not (MARKER NO. 4>MARKER NO. 1)] else [(MARKER NO. 4>MARKER NO. 1) nor (MARKER NO. 2>=MARKER NO. 3)]

If (MARKER NO. 1=MARKER NO. 5) then [not (MARKER NO. 1<MARKER NO. 4)] else [(MARKER NO. 3=MARKER NO. 2) nor (MARKER NO. 1<MARKER NO. 4)]

Preferably, the assay kit of the invention comprises software, which is programmed to comprise the above logic rules, and which can—on basis of the stochastic values 0 or 1, resulting from the hybridization test—immediately yield the result of the test, i.e. whether the tested sample contains a pathogenic *Legionella* strain or not.

EXAMPLES

DNA Isolation of Sample

In the present Example a total of 144 samples from different strains were selected from the collection of strains of the Streeklaboratorium Kennemerland in Haarlem, The Netherlands. Of these 144 samples, a total of 74 samples was isolated from hospital patients (pathogenic or clinical strains) and a total of 70 samples was isolated from industrial and public water supply systems, and were not detected in humans (environmental strains).

Labeling and Hybridisation of Genomic DNA

All strains were cultivated after which genomic DNA was isolated from these strains. The DNA was then randomly (primer) labeled using Klenow DNA polymerase (BioPrime kit Invitrogen) according to the manufacturer's instructions.

Cy3 labeled marker sequences were prepared, comprising the sequences 1a, 2a, 3a, 4a and 5a. The DNA sample consisted of the DNA of the test strain and was labeled with Cy5. Both labeled samples were hybridized simultaneously to a microarray. Upon scanning and image analysis, the ratio of the Cy5/Cy3 emission values was calculated for each spot on the microarray. These ratio's served as data input for further data analysis.

All tests showed a positive control, i.e. the presence of *L. pneumophila* DNA was detected. Then, on basis of either positive or negative hybridization signals on the two markers (MARKER NO. 1 and MARKER NO. 2) or the five markers (MARKER NO. 1 through MARKER NO. 5) a classification of the sample as 'pathogenic' or 'non-pathogenic', respectively, was generated according to the rules as shown above. For the results, the sensitivity and specificity of the tests were calculated.

Sensitivity is calculated as the number of true positive classifications divided by the sum of the number of true positives and the number of false negatives as expressed by equation 1:

$$\text{sensitivity}=TP/(TP=FN) \quad (I)$$

wherein true positives are the number of pathogenic strains correctly identified and false negatives are the number of pathogenic strains incorrectly classified as being environmental strains.

Specificity is defined as the number of true negative results divided by the sum of the true negatives and the false positives as expressed by equation 2:

$$\text{specificity}=TN/(TN+FP) \quad (II)$$

wherein true negatives are defined as the number of environmental strains that are correctly identified and false positives are defined as the number of environmental strains that are identified as being pathogenic.

| Array size | Sensitivity (%) | Specificity (%) |
|---|---|---|
| 5 markers | 95.8 | 61.4 |
| 2 markers | 86.3 | 68.6 |

MARKER NO. 1 (LePn.01gH4)

SEQ ID NO: 1
AAAGGAGACTTGGCAGCTCTCAAGAACTTGTTTGGTTGCAAGCAAAAACT

TCAACCCGGCTCTCTAATTAGCCTTGATAATACAACCTTTGCCTTTCCTT

GTAAGGGAGTTCCTACCCAATACTGGGATCTGGTAAATGGCTGGGAATTA

CAAAACAAGGTATCTATAGGTGAACCCATTAAATGGTCGGATATTAAGCA

AAAAAATGATTGTTAAAAACCCTACTTGGAACTCTCTTACCCCTCCACTT

-continued

CCTAAATTTGTTTCTTGTGATACAGGCGAGACAAATTTCCTGAAAGAAAA

ATTAGGAGAAGATGGGAGGGTTTTTATTGCTCAATTTGATCTAAAATCCA

CCTCTGCTTTTTTATTTCAGCGTAAAAGTGATCAAAAAAAATTTTTTATC

AAGAAAGTATCCGCTGAACATAAAAGACAGTATCAGCAGAGCGAACATTT

GGCTCAATTTATCGCTTGCCCAGATTATATAGTTAATATTGCAATTAACT

GCGTTTCTAATGAAGAAGAAAACTCACTCTATTATATTTATCCCTATATT

CATGGAAAACGCCTCTTTGCTGAACCAGAGGAAATAATAAGCCTTGCAAC

TGCATTAGCAAAATTACATCTTAAAAAAAAATCTTATCCTGATCAACAAT

TGATTATTAAAAATACTACGGAACGAACATCACAGCTTAATTTTATAAGA

AAGGCTTTAGCTAATGGATGTTATTCCTACATTCCATATTTCTCTTTTGT

TAAAAAGATGGCTCAACAATATGATTTTGATTGGATTAATCAAGAAGATG

CCCAACCAATTCATGGTGATTTAAATGCAGGAAATCTGTTACTATCCGAA

AATAATATGATTTGCTTTTTTGACTTTGAAGACGCATTACATAGTTTCCA

TCCAGTAGTATTAGATTTGCTATTCGTCATTGAGCGTATTATTTTTAATC

AAAATAGTTCGACTGAACGGCTATTAAACCTTGGTCTCATGTTTATTCAT

GCATATAAAAAGGCTGGTGGTACATACCGGTATAAAACGAGAGATGAATT

TGGATTAACAATTCTTGCTTTAAAAGCATTTTGCTTGTTGACTTTGCTAG

CAGAGAAAAATAAAAATATACTGAACTCGGAATGGGATAAATTTTTTAAA

TTAACTCAGAAAGCAGAAAATGAACGGGATTTAATAAAAACAATTTTACA

AGGATAAGAAAGATAGTGTGAGAGTTCTTGTTACTGCACGGGATGTTGGT

GCTGCATTAAACATTATTGAGATAGTAAAAATACTTAAACAATATACAGG

TGTTACTGTATATATTTATGCTCAACCTCCCGCTTCAAAATATTTTCTTC

GGGCTGGGATTCAATCTGTATTTCAAGTTCCACTACCACCAACCCGATCC

TCAAATGAATCCAATCATCTACTATCCTACGCCAATCAATTAATTGATAA

ATTAAATCCCGATATCATATTATCTGGATTATCATCTCCTGGCGAAGCTG

GCATAGATGAAGCAATAATAGCTGTGTGTCCCGCGCATATCAAAACATTC

ATCCTTCAAGATTTTTGGGGAGAAGTTAATTTTTTCTTTGAAAAATTAGC

GGATTGCTATTTATGCATAGATCATCACGCTGCAGAAATTACAAAAAAAC

GATTTAATGCCAAAACCAGGGTGATAGGCTCCCCTCGCCATACCATTTTC

AAACATAAAA

SEQ ID NO: 2
LOCUS CP000675 3576470 bp DNA circular BCT 24-MAY-2007
DEFINITION *Legionella pneumophila* str. Corby, complete genome.
ACCESSION CP000675
Nucleotides: 2745801-2747514
AAAGGAGTACTTGGCAGCTCTCAAAGAACTTGTTTGGTTGCAAAGCAAAA

ACTTCAACCCGGCTCTCTAATTAGCCTTGATAATACAACCTTTGCCTTTC

CTTGTAAGGGAGTTCCTACCCAATACTGGGATCTGGTAAATGGCTGGGAA

TTACAAAACAAGGTATCTATAGGTGAACCCATTAAATGGTCGGATATTAA

GCAAAAAAATGATTGTTAAAAACCCTACTTGGAACTCTCTTACCCCTCCA

CTTCCTAAATTTGTTTCTTGTGATACAGGCGAGACAAATTTCCTGAAAGA

AAAATTAGGAGAAGATGGGAGGGTTTTTATTGCTCAATTTGATCTAAAAT

-continued

CCACCTCTGCTTTTTTATTTCAGCGTAAAAGTGATCAAAAAAAATTTTTT

ATCAAGAAAGTATCCGCTGAACATAAAAGACAGTATCAGCAGAGCGAACA

TTTGGCTCAATTTATCGCTTGCCCAGATTATATAGTTAATATTGCAATTA

ACTGCGTTTCTAATGAAGAAGAAAACTCACTCTATTATATTTATCCCTAT

ATTCATGGAAAACGCCTCTTTGCTGAACCAGAGGAAATAATAAGCCTTGC

AACTGCATTAGCAAAATTACATCTTAAAAAAAAATCTTATCCTGATCAAC

AATTGATTATTAAAAATACTACGGAACGAACATCACAGCTTAATTTTATA

AGAAAGGCTTTAGCTAATGGATGTTATTCCTACATTCCATATTTCTCTTT

TGTTAAAAAGATGGCTCAACAATATGATTTTGATTGGATTAATCAAGAAG

ATGCCCAACCAATTCATGGTGATTTAAATGCAGGAAATCTGTTACTATCC

GAAAATAATATGATTTGCTTTTTTGACTTTGAAGACGCATTACATAGTTT

CCATCCAGTAGTATTAGATTTGCTATTCGTCATTGAGCGTATTATTTTTA

ATCAAAATAGTTCGACTGAACGGCTATTAAACCTTGGTCTCATGTTTATT

CATGCATATAAAAAGGCTGGTGGTACATACCGGTATAAAACGAGAGATGA

ATTTGGATTAACAATTCTTGCTTTAAAAGCATTTTGCTTGTTGACTTTGC

TAGCAGAGAAAAATAAAAATATACTGAACTCGGAATGGGATAAATTTTTT

AAATTAACTCAGAAAGCAGAAAATGAACGGGATTTAATAAAAACAATTTT

ACAAGGATAAGAAAGATAGTGTGAGAGTTCTTGTTACTGCACGGGATGTT

GGTGCTGCATTAAACATTATTGAGATAGTAAAAATACTTAAACAATATAC

AGGTGTTACTGTATATATTTATGCTCAACCTCCCGCTTCAAAATATTTTC

TTCGGGCTGGGATTCAATCTGTATTTCAAGTTCCACTACCACCAACCCGA

TCCTCAAATGAATCCAATCATCTACTATCCTACGCCAATCAATTAATTGA

TAAATTAAATCCCGATATCATATTATCTGGATTATCATCTCCTGGCGAAG

CTGGCATAGATGAAGCAATAATAGCTGTGTGTCCCGCGCATATCAAAACA

TTCATCCTTCAAGATTTTTGGGGAGAAGTTAATTTTTTCTTTGAAAAATT

AGCGGATTGCTATTTATGCATAGATCATCACGCTGCAGAAATTACAAAAA

AACGATTTAATGCCAAAACCAGGGTGATAGGCTCCCCTCGCCATACCATT

TATCAAACATTAAA

Marker No. 2

SEQ ID NO: 3

TTCTTCATTCCATCTCTGGCACCAGATTTTACCTAAAACTTCATGCCAAA

TCTTAGCAAGCTTTGGAATACAGTCTGAATATTGTTTTAGGTAGGCTATT

GTTATCATCATAATACCTGTTTAAAATGGATTATTCCTCGCACTCGTGGC

AAGGCGTTCCTTGATGAAACACCATTTGCCAACGATTGTGTTTGTATTGC

CAGAGCGAAGAACGTAAAGAACTTTTTGAGGCAACAGTAACCTTATAAGT

TGCCAACATGACTTCAGGCGACACCTCTAAAACTGAAAAATCATTAACCA

TATAGCTTCGTTGCTCTTCTTCTGGAAGAGAATCAAGTAGGTCGTTCTTA

TTGTAAATTGAGCCAGAGGCCCCATACTCGATAAATTCATCAGCAATCAA

TAGTTTCAGTTGCGCAATAGATTTTCTCGTTTCCGACCTTAATAGAGAAA

TTTCTAGCTCATAAATCAATTGGTGTTCTTGTTTCATAGCGATTTTCTCA

-continued

TCAAATAAACGTTGAAATCCAAAAAACAATTATGCTCTGTCATGGATATG

ACAACATACCCAAGCTGTTCATAAAAAGATCTTGCCTGAAATTCGGCCGT

CTCAATGGTAATCACTTGGCAATTCTTTTGTTTTGCAAAAATTTCCAGTT

TTTCCATGAGATTTCGTCCTAATCCTTTTTGTCTAAAATCCGGATGAACC

CAAATGCAATCGACATAGCAATTGGCTCGAGTGACATCCCCATAACAACC

TGCTAAAACGGTCTTGTCGATAGATTTTATATAGATGGTAAAGGGAGTAT

GATTGTAAGCACCAATCATTTCTTCATTGTAGATCTTTAAGCCGTCAGAT

AAAATGGCAGTGATTTCTTGGTTGGTTCGTTCTTCGAAACAAATCTCATA

GTCATTGTTCTTGGCTAAAATTATAAGCTCTGGTATTTTTTGCATCTTCTG

GTGCATCGGAATGATAACCGCTCCAAAGAATACCTCCATAAGGTTGTAGT

ATTTTTTCAACCAACTTTTTTAAATGAGTTGAATCACCTTCCTTATAAAC

TCGATTAAAACTTTCAGAAAACTCCCTGGCTAAATCGGGATTTTCTTGAT

GCAAATAGCGAATGATTGATTTACCACTGGCGCACCATTTATTTTGAGCT

CTAAAATAAAATTGAGACAATGCTTCAAAAAGCCATGAGGCTGAGGCAAT

TTGTTCTTCATAAGACTTAGGAGATAAAATATCTTCTAAGACATCCGTAA

TTAAAAAACGCTCTTTATCAATTTGATTTTTATCCCAAGAAAGAGGTCCG

CGCTTTAAGTAAAGATAGGCCTCCTCTCTAATCCCGTTTGAAAAATCGCT

AGCTGGCATCATATCTTTTCCCGACAAAATCATTTGAATGGTTCCTGAAA

TACCGGAATTTATTCTCGATTCTCAAAAAAATAACGAATGGTTTCT

SEQ ID NO: 4
LOCUS CR628338 131885 bp DNA linear BCT 17-APR-2005
DEFINITION *Legionella pneumophila* str. Paris plasmid pLPP, complete sequence.
ACCESSION CR628338
Nucleotides: 118745-120194

TTCTTCAATTCCAATCTCTGGCATCCAGATTTTACCTAAAACTTCATGCC

AAATCTTAGCAAGCTTTGGAATACAGTCTGAATATTGTTTTAGGTAGGCT

ATTGTTATCATCATAATACCTGTTTAAAATGGATTATTCCTCGCACTCGT

GGCAAGGCGTTCCTTGATGAAACACCATTTGCCAACGATTGTGTTTGTAT

TGCCAGAGCGAAGAACGTAAAGAACTTTTTGAGGCAACAGTAACCTTATA

AGTTGCCAACATGACTTCAGGCGACACCTCTAAAACTGAAAAATCATTAA

CCATATAGCTTCGTTGCTCTTCTTCTGGAAGAGAATCAAGTAGGTCGTTC

TTATTGTAAATTGAGCCAGAGGCCCCATACTCGATAAATTCATCAGCAAT

CAATAGTTTCAGTTGCGCAATAGATTTTCTCGTTTCCGACCTTAATAGAG

AAATTTCTAGCTCATAAATCAATTGGTGTTCTTGTTTCATAGCGATTTTC

TCATCAAATAAACGTTGAAATCCAAAAAACAATTATGCTCTGTCATGGAT

ATGACAACATACCCAAGCTGTTCATAAAAAGATCTTGCCTGAAATTCGGC

CGTCTCAATGGTAATCACTTGGCAATTCTTTTGTTTTGCAAAAATTTCCA

GTTTTTCCATGAGATTTCGTCCTAATCCTTTTTGTCTAAAATCCGGATGA

ACCCAAATGCAATCGACATAGCAATTGGCTCGAGTGACATCCCCATAACA

ACCTGCTAAAACGGTCTTGTCGATAGATTTTATATAGATGGTAAAGGGAG

TATGATTGTAAGCACCAATCATTTCTTCATTGTAGATCTTTAAGCCGTCA

GATAAAATGGCAGTGATTTCTTGGTTGGTTCGTTCTTCGAAACAAATCTC

-continued

ATAGTCATTGTTCTTGGCTAAAATTATAAGCTCTGGTATTTTTGCATCTT

CTGGTGCATCGGAATGATAACCGCTCCAAAGAATACCTCCATAAGGTTGT

AGTATTTTTTCAACCAACTTTTTTAAATGAGTTGAATCACCTTCCTTATA

AACTCGATTAAAACTTTCAGAAAACTCCCTGGCTAAATCGGGATTTTCTT

GATGCAAATAGCGAATGATTGATTTACCACTGGCGCACCATTTATTTTGA

GCTCTAAAATAAAATTGAGACAATGCTTCAAAAAGCCATGAGGCTGAGGC

AATTTGTTCTTCATAAGACTTAGGAGATAAAATATCTTCTAAGACATCCG

TAATTAAAAAACGCTCTTTATCAATTTGATTTTTATCCCAAGAAAGAGGT

CCGCGCTTTAAGTAAAGATAGGCCTCCTCTCTAATCCCGTTTGAAAAATC

GCTAGCTGGCATCATATCTTTTCCCGACAAAATCATTTGAATGGTTCCTG

AAATACCGGAATTTATTCTCGATTCTTCAAAAAAATAACGAATGGATTCT

Marker No. 3

SEQ ID NO: 5
CAGCTGATTCGTTTTTCTGGGATATGTCTTGGCATGCAGATGATGCTTTC

CAAAGTACTGAATTTGGACAACATGAAGGTCTGGGTCTAATTGCTGGCGA

GGTTGTTAGCGTCCCTTCACATGGAGTTGATGGTCAATTGCATAAAATAC

CTCATATAGGCTGGAATGAACTGGTTTCCACCTCGGAAGGCGAGGATTGG

TGTCATACTATCCTGAAAAATATACCATTAAATTCTTCAGTATATTTTGT

TCATTCTTTTATGGCCATGCCTAGTAATCCTAAAAAGCGTCTGGCTGATA

CTTTATATGATGGTCAGGCTATTAGCGCAGTAATAAAAGATGAAAATATG

TACGGATGCCAATTTCATCCTGAAAAAAGCGGGGAAGTAGGTTTAAGCAT

CATTCAACAGTTTTTGCAGATTTAGGGTGAATTAAAAATGAGAATATTGG

CAGTAATCCCGGCAAGGGCTGGCTCAAAGAGGCTGCCCGGTAAAAATACC

AGATTACTTGCCGGAAAACCATTAATTGCACATACTATTGTTGCTGCCTT

GCAGTCGTCTTGTTGTGAAGAAATCGTTGTTTCGACCGATAGTAAACAAA

TAGCAGACGTCGCAGTTCAATATGGGGCTTCAGTACCCTGGCTAAGATCG

GAAGATTTAGCCACGGATACTTCGGATGTGATTCATACTGTTATTGACCT

CCTGTTTAAGTTTCAGCAAATGGAGGTTTTTTTTGACAGTGTATTGCTGT

TACAACCAACTTCTCCATTTAGGAAGCCAGAAACCATAAGACATGCTGTT

GAAATACATCAAGTAACGGGGAAAAGTGTCGTTTCAGTTAGTCCCATCTC

TTTAAAGCCTTCTTGGTGTAGAAGCATTGATAGCCAAGGCA

SEQ ID NO: 6
LOCUS CP000675 3576470 bp DNA circular BCT 24-MAY-2007
DEFINITION *Legionella pneumophila* str. Corby, complete genome.
ACCESSION CP000675
Nucleotides: 2763054-2763893
TGCCTTGGCTATCAATGCTTCTACACCAAGAAGGCTTTAAAGAGATGGGA

CTAACTGAAACGACACTTTTTCCCGTTGCTTGATGTATTTCAACAGCATG

TCTTATGGTTTCTGGCTTCCTGAATGGAGAAGTTGGTTGTAAAAGCAATA

CACTGTCAAAAAAAACCTCCATTTGCTGAAACTTAAACAGGAGGTCAATA

ACAGTATGAATCACATCCGAAGTATCCGTGGCTAAATCTTCCGATCTTAG

CCAGGGTACTGAAGCCCCATATTGAACGGCGACGTCTGCTATTTGTTTAC

-continued

TATCGGTCGAAACAACGATTTCTTCACAACAAGACGACTGCAAGGCAGCA

ACAATAGTATGTGCAATTAATGGTTTTCCGGCAAGTAATCTGGTATTTTT

ACCGGGCAGCCTCTTTGAGCCAGCCCTTGCCGGGATTACTGCCAATATTC

TCATTTTTAATTCACCCTAAATCTGCAAAAACTGTTGAATGATGCTTAAA

CCTACTTCCCCGCTTTTTTCAGGATGAAATTGGCATCCGTACATATTTTC

ATCTTTTATTACTGCGCTAATAGCCTGACCATCATATAAAGTATCAGCCA

GACGCTTTTTAGGATTACTAGGCATGGCCATAAAAGAATGAACAAAATAT

ACTGAAGAATTTAATGGTATATTTTTCAGGATAGTATGACACCAATCCTC

GCCTTCTGAGGTAGAAACCAGTTCATTCCAGCCTATATGAGGTATTTTAT

GCAATTGACCATCAACTCCATGTGAAGGGACGCTAACAACCTCGCCAGCA

ATTAGACCCAGACCTTCATGTTGTCCAAATTCAGTACTTTGGAAAGCAT

CATCTGCATGCCAAGACATATTCCCAGAAAA

Marker No. 4

SEQ ID NO: 7
ATACACCGCCGCCCATGAGCCGTTCAAAGCTGTAGTGAAGTATTTACAAG

AGCATATCAGTAAAGCCATCACTTCAGGCAACGTTGAAAGCCTTCATGAT

CAAGTGCTCATTGATCTGTTTGATGCGGCCATTATGGATAAAAATTATTA

CGATAAAATCACAGCCAGTGTTGGCCCTGTATTATCAGAGATTAATAAGA

GTAATGCCTCCAGGATCTTTTCATTTCATAAAAGCAATTGTGAAATCGAG

TTGATGAGTGCAATAAAAAACAAACAAGTCATCTATATCGGGCTGGATAG

CTTAACAAACCCCAATATCGCTCAAGCAGTCGGTAAAGCCTTTTTGTCAG

ATTTAGTATCCACTGCTGGAAAAATATATAAGGAAAGTAACGCGAATTAC

CGTCTCAATCTCCATTGCGATGAGCTTTCTGAAATTATCCAAGATTCGTT

TGTTAAAATTTTAAATAAAGCCGGTGGAGCTGGTTTCCAAGTCACAGCTT

ATGCTCAGACCAAACAAAATATGGAGGTAGCGCTAGGTTCAAAAGCCAAA

GCAGAAGTGACTGAAGGAAATCTAAACACCCTCATCATGTTACGTGTCAA

AAATGAAGAAACTGCCAATTTATTAGNTTAAAGTTTTACCAAAAATTTGG

CGTGGTCGAACATACTCAAGTCTCCATGGTCAACGACACACCCCATGGCG

AAGATGGGCGTTTATTTTANCACCACCAATGAAGATCGTGTACAAACCAC

CGCAGTGCCGATGAATTGATGTNCATGACATTATCTCATTACCCCAAGGG

CAAGCATTTTGTTTTAGTGAATGGGCGGAAGAACTGTACAAAGTAAGAAT

ACCCTTACCCTGTGACGATGGATTAGCCCCCAAGGGATATCAAAAGCGCT

ATTCGTGTAATTAACCAAATTGGATGATAACCTTGGAGATTAATATGAAA

GCAGAAATTACTTTAAACCCTTCGTACCCGTGAAGTGTACAAGTTATTTG

AAAGAAAGATTAATGAGGATAGATTATTTATTGA

SEQ ID NO: 8
LOCUS CP000675 3576470 bp DNA circular BCT 24-MAY-2007
DEFINITION *Legionella pneumophila* str. Corby, complete genome.
ACCESSION CP000675
Nucleotides: 2091357-2092380
ACGGAAATACACCACCGCCCATGAGTCGTTCAAAATCTGTGGTGAAGTAT -continued

TTACAAGAGCATATCAGTAAAGCCATCACTTCAGGCAATGTTGAAAGCCT

TCATGATCAAGTACTCATTGATCTGTTTGATGCTGCCATCATGGACAAAA

ATTATTACGATAAAATCACGGCCAGTGTCGGCCCTGTGTTATCAGAAATT

AATAAAAGTAATGCATCAAAGATCTTTTCATTTCATAAAAGCAATTGTGA

AATCGAGTTGATGAGTGCAATAAAAAACAAACAAGTCATTTATATCGGAC

TGGATAGCTTAACAAACCCCAATATCGCCCAAGCAGTAGGTAAAGCCTTT

TTGTCAGATTTAGTATCCACAGCTGGAAAAATATATAAGGAAAGTAACGC

GAATTACCGTCTCAATCTCCATTGCGATGAACTTTCTGAAATCATCCAAG

ACTCATTTGTCAAAATTTTAAATAAAGCCGGTGGAGCTGGTTTTCAAGTC

ACCGCTTATGCTCAGACCAAACAAGATATGGAGGTGGCATTAGGCTCTAA

AGCCAAAGCAGAAGTGACTGAAGGAAATCTAAATACGCTCATCATGTTAC

GTGTTAAAAATGAAGAAACAGCCAATTTATTAGTTAAAGTGTTACCAAAA

ATTGGCGTGGTCGAGCACACTCAAGTGTCCATGGTCAACGACACACCCCA

TGGCGAGGATGGCGTTTATTTTAACACCACCAATGAAGATCGAGTACAAA

CCACCGCAGTACCTATGATTGATGTCAATGACATTATCTCATTGCCCAAA

GGGCAAGCCTTTGTTTTAGTGAATGGCGGAGAGCTGTACAAAGTAAGAAT

ACCCTTACCTGTGAACGATGGATTAGCCCCCAAGGATATCAAAAGCGCTA

TTCGTGCAATTAACCAATTGGATGATAACCTTCGAGATTAATATGAAAGC

AGAAATTACTTTAAACCTTCGTACCCGTGAAGTGTATAAATTATTTGAGA

GGAAAATTAGTGGGGATAGGTTATTTATTGA

SEQ ID NO: 9

ATTGCGGGTTAAATATTTTACTGAATCGCAAACCACTTAATAACGATAAG

AAGCCCGATACCAAAACACCCATGACGCATACTTGGCCAACACCTGCTGA

TGCCAGTAAATGGGCAGTTAAAGTATTAGGTGATATTCATGTAAGCACCG

CTACAGATGCAGATAAAACCAAACACGATGCCAAAGCTGGCATTGGATTA

TCCGCGTTATTGCAAAGTTGTGACAGCTCCAACACCTGTACTTCAAATGT

GTCTAAAGCACTGTGGAATCTAGTAGACAAGCAATGGCCGTTGACTGAAG

AAAAACTCAAAATGGTTAGTGCATCCAACTTGATGATTACAGATGAAATT

ATCATCACCATACAACGTATGCCGCGGGAAGAGCAAATTTTAACTGTTTC

CAAATTGGCTGAGGAAATTGCTGTACAAAACATGCTCGATAAGGCCTTGA

TGATGCGCCGTATCTTACAAGCTGGTCTTCAAGTACAAGAAGTACAAAAC

TTAAAGCCCGCGCTTGATATGGTGAAATTTG

SEQ ID NO: 10

CGTTCGAAAAACCACCAGATGCCATAGGTATTGCAGGAATATCCCTATTA

TAAACAGACCGCAAATACTGCCTAACGCCTTAGGGTTATAACCACTTAGA

GCCAAAATCACAGGAGTCAATATAATCAGGAAGAAATACAAAAAGGCCTG

CATGACAGGTAGTGTTTGCATAATAGCTTCACGCTTTAATGGCGTTGATG

TCCATGATTTTGTTAATTGCCCAATATTTACTAACCCATGAGAAATGGCA

CCACCAAAAGCCCCATTAGTGTTTCCCATTAGGTTTTTCATACTGTTAGC

CTGCATGTCGCGACTGTCATTAAGCAACATCTTGGCAATGTAGTCTTCTG

AGCTTAACTGCGAACCCCAGGCTTTGGGATGGTCATTTTTGAATGTGCGT

ACCCTGTCTAAAACCGCGTAGTAATTCAGGTGGCTGTCAAAGACACTGGC

-continued

GTTATTGGCTACTTGCACCAAATCTGTTTTGAGCTTTTTCCACCATTGAT

TGCAGGTGGGATAGCCTTGCTCTGGC

SEQ ID NO: 11
LOCUS CP000675 3576470 bp DNA circular BCT 24-MAY-2007
DEFINITION *Legionella pneumophila* str. Corby, complete genome.
ACCESSION CP000675
Nucleotides: 2087422-2089476

ATTGCGGGTTACAATATTTTACTGAATCGCAAACCACTTAATAATGAAAA

GAAGCCCGATACTAAAACACCCATGACGCATACTTGGCCAACACCTGCTG

ATGCCAGTAAATGGGCAGTTAAAGTATTAGGTGATATTCATGTAAGCACC

GCTACAGATGCAGATAAAACCAAACACGATGCCAAAGCTGGCATTGGATT

ATCCGCGTTATTGCAAAGTTGTGACAGCTCCAACACCTGTACTTCCAATG

TGTCTAAAGCACTGTGGAATCTAGTAGACAAGCAATGGCCGTTGACTGAA

GAAAAACTCAAAATGGTTAGTGCATCCAACTTGATGATTACAGATGAAAT

CATCATCACCATACAACGTATGCCGCGGGAAGAACAAATCTTAACTGTTT

CCAAATTGGCCGAGGAAATTGCTGTACAAAACATGCTCGATAAGGCCTTG

ATGATGCGCCGTATTTTACAAGCTGGTCTTCAAGTACAAGAAGTACAAAA

CTTAAAGCCCGCGCTTGATATGGTGAAATTTGCCTTAAAGAAACTCGATG

ATGACATTCATTCTTTATCTTTTGAAAGCGAAGTCCGTAAAAAAATGATG

ACTGAAACCTTAGGTCTTTTGATGGATATGCGAGGTAGCGATATAGCCAA

GGGCTTGCCTGGTGAAGATCATGAACAATCGCAAGTTAAAAATGGCGCAG

TCTATGCGAAACCTGATTCCAAAGGAGCATAAGATGGTTGTATTTAGCCC

TTTATCCTTGTACACCACCTATTTAGGCTGGCAGCAATATGAGGTTATTT

TTAATGCCCTGTGGCAAACCGGTTTGTTATACCTTGGTTTTCTTATGGTA

GGGTATCGATTCTTAAAAAATGTGCTGGCACCTTCTGGTGCTACACATCA

CGCGGCAGAATATGCCTTGAATCATTTTCTTTATGAATTGGCAATTACTT

TTTTGATTTGCGGCATCTTTATCTACCCCTGTGTGCCATTGGAAGAAAAA

GCCATGAGTTTTAAGCCTATGTGCGGTATAAAAAAAGGAACAGATGCAAA

AACCTCTACGTTAAAAGATACAGGTACTACTTATGATGAAGCATTTGCAG

ACGTACTGACCCCCAATGTCAAAATGCCTATTGGTTTTGCACTCTTGCAA

AATTACATGTCAGGGATTACCTACGGCTTGATGAAAGTGACCGGTTGCAC

CGACAGCTTACAAGCAATTGAAGGCGATTTAATTTCCACCTATTTACCTG

CCGATGTACGTGAGCAAGCATTGAATTTTCACAGACAATGCTTCCTTGAG

GCCAGAAGCCAATATCACAATGAACCGCACGATAAAACTAAGGTCAATGA

CATTTTAAAAAAATACGGTGGTGAGGAAGATTTGAAATGGGTGGGTTCCA

AAGTCTATCAAACACTATACTATGATAAAATTTACGCAAGACAACCCGTA

GCTGGCTTTACCTTTAACGAAGCCCCCAACAAAAATCTCGAAAAAGCAGC

AGAACGTGGTGATATTGATGCCAAACATCTGCCAGAGCAAGGCTATCCCA

CCTGCAATCAATGGTGGAAAAAGCTCAAAACAGATTTGGTGCAAGTAGCC

AATAACGCCAGTGTCTTTGACAGCCACCTGAATTACTACGCGGTTTTAGA

CAGGGTACGCACATTCAAAAATAACCATCCCAAAGCCTGGGGTTCGCAGT

TAAGCTCAGAAGACTACATTGCCAAGATGTTGCTTAATGACAGTCGCGAC

-continued

ATGCAGGCTAACAGTATGAAAAACCTAATGGGAAACACCAATGGGGCTTT

TGGTAGTGCCATTTCTCATGGGTTAGTAAATATTGGGCAATTAACAAAAT

CATGGACATCAACGCCATTAAAGCGTGAAGCCATTATGCAAACGCTACCT

GTCATGCAGGCTTTTTTGTATTTCTTCCTGATTATCTTGACTCCTGTGAT

TTTGGCTCTAAGTGGTTATAACCCTAAGGCGTTAGGCAGTATTTGCGGTC

TGTTTATCATGGCGATTTTCCTGCAATACCTGTGGCATCTGGTGGGTTTT

GTCGA

Marker No. 5

SEQ ID NO: 12
ATAAAGAGATATTTCTTTGCGCAATGCAAAGTAGTCAAGCATTACATCAT

CNTTGGGTTAAAGCGCCTGTAACACCTGATGAGTTTGATGAGTATTTTTC

TCGCTATCAAAAACCCAAACCCAAAAAAGTTTCTGCTTTTTTCTGCCAAT

AACTTAGCGGGCGTCTTTAATATCAGCGAAATAGTACGTGGTTACTTTCA

AAATGCGTATTTGGGGTTTTATGCTGTTGAGGCTCATGCGGGTAAAGGAT

ACATGAGTAAGGGTTTAAAATTAATATTAACCAGGATTTTTAAGGAAATG

GGGTTGCATCGGTTAGAGGCGAATATACAACCTGAAAATAACCGTTCAAT

CTGGCTGGTGAAGAAAAATGGTTTTCGTTATGAAGGATTTTCTCCACGTT

ATTTGAGGGTGAATGATGTGTGGCAAGGTCATGAGCATTGGGCCATGACT

TATGAAGATTTTATCAAGGATAATAATGATGTGCTTGAAAAAGATCATAT

CGACATTGTTGCCTATAATACCGAGTGGCCACTGCTAGCTAAAATAGAAA

TGGCGAAATTACGCGCTTCATTTCCAGCCAATAGTGTGATTGATGTCCAG

CATGTGGGTAGTACAGCAATACCTGGCATGGCAGCAAAACCCATTATTGA

TATTCAGATTGCAGCCAGGTCATTGGAGGAAATGAAGATTATTGCTGTGC

CGATATTACAGAAATTAGGTTATGAATATTGGGAAGATAATCCGGACTCT

-continued

GAACGAATGTTCTTTGTAAAAGGCATGCCACCCTATGGTAATGGGCGAAC

ACACCATGTTCATATTGTTGAAACATCATCCAGGCATGGAAAGGAAAGAT

ACTTTCAGAGACTATT

SEQ ID NO: 13
LOCUS AE0173543 397754 bp DNA circular BCT 14-SEP-2006
DEFINITION *Legionella pneumophila* subsp. *pneumophila* str. Philadelphia 1, complete genome.
ACCESSION AE017354
Nucleotides: 554886-555752
ATAAAGAGATGTTTCTTTGTGCTATGCAAAGTAGTCAAGCATTACATCAT

CCTTGGGTTAAGGCACCGATAATACCTGAAGAGTTTGATGAGTATTTTTC

TCGCTATCAAAAACCAAACCAAAAAAGCTATCTGCTTCTTTCTGACAATA

ACTTAGCGGGTGTCTTTAATATCAGTGAAATAGTACGTGGTTACTTTCAG

AATGCGTATTTGGGGTTTTATGTTGTTGCAGCTTATGCGGGTAAAGGATA

TATGAGTACTGGTTTGAAATTAATATTAACCAAAGTTTTTAAGGACATGG

GGTTGCATCGCTTAGAAGCGAATATACAACCTGAGAATACCCCTTCAATC

TGGCTTGTGAAGAAAAATGGTTTTCGCTATGAAGGATTTTCCCCACGATA

TTTGAGAGTGAATGACGTGTGGCAAGGTCATGAGCATTGGGCCATGACTT

ATGAAGATTTTATCAAGGATAATAATGAGGTACTTGAAAAAGATCATATC

GATATTGTTGCATACAATACAGAGTGGCCGCTTCTAGCCAAGGCAGAAAT

GGTGAAGTTACGCGCCTGATTTCCCGCAAATAGTGTTATTGATATCCAGC

ATGTAGGCAGTACAGCAATACCTGGCATGGCATCAAAACCCATTATTGAT

ATTCAGATTGCAGTGAGGTCATTAGAAGAAATGAACATTATTGCTGTGCC

GATATTACAGAAATTAGATTATGAATATTGGGAAGATAATCCAGATCCTG

AACGAATGTTTTTTGTAAAAGGCATGCCCCCCTATGGTAATGGACGAACG

CACCATGTTCATATCGTCGAAGCATCATCCAGGCATTGGAAAGGAAAAAC

ATTTTTCAGAGACTATT

The invention claimed is:

1. A method to determine whether a *Legionella pneumophila* strain is a pathogenic strain or a non-pathogenic strain in a sample containing *Legionella pneumophila*, wherein said method comprises the steps of:

a) subjecting said sample to an assay that detects the presence or absence in said sample of at least one of a first polynucleotide comprising the sequence of SEQ ID NO:1 or 2 or that comprises a sequence that has at least 95% identity with SEQ ID NO:1 or 2;

b) subjecting said sample to an assay that detects the presence or absence in said sample of a at least one of second polynucleotide comprising the sequence of SEQ ID NO:3 or 4 or that comprises a sequence that has at least 95% identity with SEQ ID NO:3 or 4; and c) determining that said strain is pathogenic if the first polynucleotide is present and the second polynucleotide is absent, or determining that said strain is non-pathogenic if the first polynucleotide is absent and the second polynucleotide is present.

2. The method of claim 1, wherein the assays are performed by hybridizing DNA of said sample with a probe complementary to at least 50 nucleotides of the sequences of SEQ ID NOS:1-4 or sequences of at least 95% identity thereto.

3. The method of claim 2, wherein the assays are performed by hybridizing the DNA of said sample with a probe complementary to at least 500 nucleotides of the sequences of SEQ ID NOS:1-4 or sequences of at least 95% identity thereto.

4. The method of claim 3, wherein the assays are performed by hybridizing the DNA of said sample with a probe complementary to at least 1000 nucleotides of the sequences of SEQ ID NOS:1-4 or sequences of at least 95% identity thereto.

5. The method of claim 1 wherein further detection steps d), e) and f) are present, wherein said steps comprise:

d) subjecting said sample to an assay that detects the presence or absence in said sample of at least one of a third polynucleotide comprising the sequence of SEQ ID NO: 5 or 6 or a sequence that has at least 95% identity therewith;

e) subjecting said sample to an assay that detects the presence or absence in said sample of at least one of a fourth polynucleotide comprising the sequence of SEQ ID NO: 7, 8, 9, 10 or 11 or a sequence that has at least 95% identity therewith;

f) subjecting said sample to an assay that detects the presence or absence in said sample of at least one of a fifth polynucleotide comprising the sequence of SEQ ID NO: 12 or 13 or a sequence that has at least 95% identity therewith; and wherein step c) further comprises:

determining that said strain is pathogenic if 4 or more of the logic rules (1)-(7) have the result TRUE, wherein said logic rules (1)-(7) are:

(1) if (MARKER NO. 2<MARKER NO. 1) then [not (MARKER NO. 2=MARKER NO. 3)] else [(MARKER NO. 2=MARKER NO. 4) and (MARKER NO. 5=MARKER NO. 3)]

(2) if (MARKER NO. 2<MARKER NO. 3) then [not (MARKER NO. 1<MARKER NO. 4)] else [(MARKER NO. 5>MARKER NO. 2) nor (MARKER NO. 5<MARKER NO. 4)]

(3) if (MARKER NO. 2<MARKER NO. 3) then [not (MARKER NO. 4<MARKER NO. 1)] else [(MARKER NO. 3<MARKER NO. 5) nor (MARKER NO. 4>MARKER NO. 5)]

(4) if (MARKER NO. 1=MARKER NO. 5) then [ (MARKER NO. 4<=MARKER NO. 1)] else [(MARKER NO. 1<MARKER NO. 4) nor (MARKER NO. 3=MARKER NO. 2)

(5) if (MARKER NO. 1=MARKER NO. 5) then [ (MARKER NO. 5>=MARKER NO. 4)] else [(MARKER NO. 3<=MARKER NO. 2) nor (not (MARKER NO. 4<MARKER NO. 1))]

(6) if (MARKER NO. 1=MARKER NO. 5) then [not (MARKER NO. 4>MARKER NO. 1)] else [(MARKER NO. 4>MARKER NO. 1) nor (MARKER NO. 2>=MARKER NO. 3)]

(7) if (MARKER NO. 1=MARKER NO. 5) then [not (MARKER NO. 1<MARKER NO. 4)] else [(MARKER NO. 3=MARKER NO. 2) nor (MARKER NO. 1<MARKER NO. 4)], wherein MARKER NO. 1 has the stochastic value 1 if at least one of said first polynucleotides is present in said sample and has the stochastic value 0 if neither of said first polynucleotides are present;

wherein MARKER NO. 2 has the stochastic value 1 if at least one of said second polynucleotides is present in said sample and has the stochastic value 0 if neither of said second polynucleotides are present;

wherein MARKER NO. 3 has the stochastic value 1 if at least one of said third polynucleotides is present in said sample and has the stochastic value 0 if neither of said third polynucleotides are present;

wherein MARKER NO. 4 has the stochastic value 1 if at least one of said fourth polynucleotides is present in said sample and has the stochastic value 0 if none of said fourth polynucleotides are present; and wherein MARKER NO. 5 has the stochastic value 1 if at least one of said fifth polynucleotides is present in said sample and has the stochastic value 0 if neither of said fifth polynucleotides are present.

* * * * *

UNITED STATES PATENT AND TRADEMARK OFFICE

CERTIFICATE OF CORRECTION

| | |
|---|---|
| PATENT NO. | : 8,415,105 B2 |
| APPLICATION NO. | : 12/521119 |
| DATED | : April 9, 2013 |
| INVENTOR(S) | : Schuren et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 645 days.

Signed and Sealed this
Third Day of March, 2015

Michelle K. Lee

Michelle K. Lee
*Deputy Director of the United States Patent and Trademark Office*